(12) United States Patent
Bull et al.

(10) Patent No.: US 12,385,843 B2
(45) Date of Patent: Aug. 12, 2025

(54) SYSTEMS AND METHODS FOR HEMOSTATIC ANALYSIS

(71) Applicant: LOMA LINDA UNIVERSITY PATHOLOGY MEDICAL GROUP, INC., Loma Linda, CA (US)

(72) Inventors: Brian S. Bull, Loma Linda, CA (US); Karen Hay, Loma Linda, CA (US); John F. Wetteland, Loma Linda, CA (US)

(73) Assignee: LOMA LINDA UNIVERSITY PATHOLOGY MEDICAL GROUP, INC., Loma Linda, CA (US)

( * ) Notice: Subject to any disclaimer, the term of this patent is extended or adjusted under 35 U.S.C. 154(b) by 707 days.

(21) Appl. No.: 17/756,496

(22) PCT Filed: Nov. 27, 2020

(86) PCT No.: PCT/US2020/070825
§ 371 (c)(1),
(2) Date: May 26, 2022

(87) PCT Pub. No.: WO2021/108811
PCT Pub. Date: Jun. 3, 2021

(65) Prior Publication Data
US 2023/0003658 A1    Jan. 5, 2023

Related U.S. Application Data

(60) Provisional application No. 62/941,589, filed on Nov. 27, 2019.

(51) Int. Cl.
*G01N 21/64* (2006.01)
*A61B 6/00* (2024.01)
(Continued)

(52) U.S. Cl.
CPC ............ *G01N 21/82* (2013.01); *G01N 35/04* (2013.01); *G06T 7/0016* (2013.01);
(Continued)

(58) Field of Classification Search
CPC ................... G01N 21/82; G01N 35/04; G01N 2035/0406; G01N 2201/062;
(Continued)

(56) References Cited

U.S. PATENT DOCUMENTS

| 2008/0317326 A1 | 12/2008 | Svanberg et al. |
| 2010/0066996 A1 | 3/2010 | Kosaka et al. |

(Continued)

FOREIGN PATENT DOCUMENTS

| JP | 2003-508060 A | 3/2003 |
| WO | 2018044328 | 3/2018 |

OTHER PUBLICATIONS

European Patent Office, Partial Supplementary Search Report for EP Application No. 20891622.1, Nov. 24, 2023.
(Continued)

*Primary Examiner* — Jennifer Wecker
*Assistant Examiner* — Oyeleye Alexander Alabi
(74) *Attorney, Agent, or Firm* — Womble Bond Dickinson (US) LLP

(57) ABSTRACT

Systems and methods for analysis of a whole blood sample from an individual to determine the platelet function and coagulation status of the individual in a substantially automated and efficient matter. Also provided here are systems, reagent kits, and methods for concurrent assessment of platelet function and coagulation as they interact during hemostasis.

20 Claims, 20 Drawing Sheets

(51) Int. Cl.

| | | |
|---|---|---|
| *A61B 8/00* | (2006.01) | |
| *B01F 23/00* | (2022.01) | |
| *B01F 23/41* | (2022.01) | |
| *B01F 101/23* | (2022.01) | |
| *B23Q 17/24* | (2006.01) | |
| *C07K 14/705* | (2006.01) | |
| *C12M 1/34* | (2006.01) | |
| *C12Q 1/04* | (2006.01) | |
| *C12Q 1/18* | (2006.01) | |
| *C12Q 1/686* | (2018.01) | |
| *G01N 1/31* | (2006.01) | |
| *G01N 15/10* | (2024.01) | |
| *G01N 21/3577* | (2014.01) | |
| *G01N 21/359* | (2014.01) | |
| *G01N 21/39* | (2006.01) | |
| *G01N 21/45* | (2006.01) | |
| *G01N 21/77* | (2006.01) | |
| *G01N 21/78* | (2006.01) | |
| *G01N 21/82* | (2006.01) | |
| *G01N 27/414* | (2006.01) | |
| *G01N 27/62* | (2021.01) | |
| *G01N 30/12* | (2006.01) | |
| *G01N 30/68* | (2006.01) | |
| *G01N 30/70* | (2006.01) | |
| *G01N 30/72* | (2006.01) | |
| *G01N 30/88* | (2006.01) | |
| *G01N 33/00* | (2006.01) | |
| *G01N 33/18* | (2006.01) | |
| *G01N 33/50* | (2006.01) | |
| *G01N 33/53* | (2006.01) | |
| *G01N 33/543* | (2006.01) | |
| *G01N 33/68* | (2006.01) | |
| *G01N 33/74* | (2006.01) | |
| *G01N 35/00* | (2006.01) | |
| *G01N 35/04* | (2006.01) | |
| *G01N 35/10* | (2006.01) | |
| *G06K 7/10* | (2006.01) | |
| *G06K 7/14* | (2006.01) | |
| *G06K 19/06* | (2006.01) | |
| *G06K 19/07* | (2006.01) | |
| *G06T 7/00* | (2017.01) | |
| *G06T 7/90* | (2017.01) | |
| *G16H 10/40* | (2018.01) | |
| *G16H 10/60* | (2018.01) | |
| *G16H 30/40* | (2018.01) | |
| *G16H 50/20* | (2018.01) | |
| *G16H 80/00* | (2018.01) | |
| *H01J 49/00* | (2006.01) | |
| *H04M 17/00* | (2024.01) | |
| *H10K 10/46* | (2023.01) | |
| *H10K 85/00* | (2023.01) | |
| *H10K 85/20* | (2023.01) | |

(52) U.S. Cl.
 CPC ............ *G01N 2035/0406* (2013.01); *G01N 2201/062* (2013.01); *G01N 2201/1222* (2013.01); *G06T 2207/30104* (2013.01)

(58) Field of Classification Search
 CPC .......... G01N 2201/1222; G01N 15/01; G01N 15/075; G01N 15/06; G01N 2015/0092; G01N 2015/018; G01N 2035/00346; G01N 2333/75; G01N 33/4905; G06T 7/0016; G06T 2207/30104
 See application file for complete search history.

(56) References Cited

U.S. PATENT DOCUMENTS

| | | | |
|---|---|---|---|
| 2011/0065193 A1* | 3/2011 | Kitagawa | ......... G01N 35/00732 422/67 |
| 2014/0270458 A1 | 9/2014 | Smith et al. | |
| 2015/0241457 A1 | 8/2015 | Miller | |
| 2017/0131198 A1 | 5/2017 | Morrison et al. | |

OTHER PUBLICATIONS

International Search Report and Written Opinion for PCT Application No. PCT/US20/70825, Apr. 1, 2021.
European Patent Office, Extended European Search Report for EP application No. 20891622.1, Feb. 16, 2024.

\* cited by examiner

SYSTEMS AND METHODS FOR HEMOSTATIC ANALYSIS

CROSS REFERENCE TO RELATED APPLICATIONS

This application is a U.S. National Phase Under 35 U.S.C. § 371 of International Application No. PCT/US2020/070825, titled "SYSTEMS AND METHODS FOR HEMOSTATIC ANALYSIS," filed Nov. 27, 2020, which is a PCT application claiming priority to and the benefit of U.S. Provisional Application No. 62/941,589, titled "SYSTEMS AND METHODS FOR HEMOSTATIC ANALYSIS," filed Nov. 27, 2019, which is incorporated herein in its entirety by reference.

INCORPORATION BY REFERENCE

U.S. Provisional Patent Application No. 62/941,589, filed on Nov. 27, 2019, is specifically incorporated by reference herein as if set forth in its entirety.

TECHNICAL FIELD

The present disclosure generally relates to systems and methods for analysis of blood samples, and in particular to systems and methods for analyzing the different aspects of hemostasis in an individual's whole blood.

BACKGROUND

Hemostasis in the human body occurs when the coagulation cascade is initiated as when blood contacts an abnormal surface, such as metal, glass or injured tissue, or when platelets are activated, such as due to damage or injury to a patient's vascular system. These events cause the generation of thrombin from the coagulation cascade and/or cause the platelets to aggregate to form a platelet plug. This platelet plug seals the hole in the damaged vasculature and, at the same time, the activated coagulation cascade leads to the formation of thrombin within and around the platelet plug that transforms fibrinogen within the blood into insoluble fibrin. Fibrin rapidly polymerizes to form a web of interlocking fibrin strands that stabilize and extend the platelet plugs to prevent further loss of blood. It is this interplay between platelet aggregation and coagulation that defines normal hemostasis or clotting. However, to the extent such platelet aggregation continues or expands beyond normal hemostasis, it can lead to thrombosis, which is the formation or presence of a blood clot or clots within a blood vessel, such as a vein or an artery. Thrombosis can lead to serious complications, such as deep vein thromboses (DVTs) pulmonary embolisms (PEs), heart attacks, or thrombotic strokes.

Both bleeding and thrombosis are serious and can be life threatening. As people age, thrombosis accounts for a high proportion of disability and death, from DVTs, PEs, heart attacks and strokes, or other vascular conditions. Therefore, it is important for patients, especially those with high risk factors, to undergo screening or testing to detect early signs of actual thrombosis, or of a thrombotic tendency, so that preventative and remedial measures can be taken. Additionally, for patients undergoing surgical procedures, especially in emergency situations, it is important to test for potential bleeding, clotting, or other issues that could cause problems during such surgery. For example, in the transplantation of a heart, liver, or other organ/tissue, it is important to prevent the patient from bleeding to death during surgery. But, because there is a new transplanted organ or tissue, there is also a higher potential for clotting as the hemostatic mechanism of the patient attempts to heal the perceived injury or damage to the patient's body due to the new tissue or organ being introduced. Therefore, although the prevention of bleeding is crucially important, it is equally important to mitigate any excessive or premature clotting. The blood screening tests currently available are primarily qualitative, lack sensitivity, and are largely directed towards detection of bleeding disorders. The more quantitative tests can be more complex to perform, and often require specialized training or education by experienced medical personnel to conduct the tests. These tests can be too time-consuming to provide rapid results as may be needed for emergency surgeries. There is a need for rapid determination of the status of patients, who have suffered severe trauma and have been transfused with blood, blood products, or large quantities of normal saline. Medical personnel need to rapidly determine the coagulation and platelet function status of these patients and which additional transfusions might be indicated. A need exists for systems and methods for analysis of hemostasis that address the foregoing and other related and unrelated problems in the art.

SUMMARY

Described here are systems and methods for hemostatic analysis of whole blood samples to determine platelet function and coagulation competency in a substantially automated and efficient matter, which can be performed in a non-invasive manner and without necessarily requiring specialized training for operation thereof. In an embodiment, the systems and methods provide for both laboratory and point-of-care testing for platelet function and coagulation analysis of whole blood samples. Described here are systems, reagent kits, and methods for concurrent assessment of both platelet function and coagulation as they interact during hemostasis.

In an embodiment, a system for analysis of blood samples contains a frame defining an analysis chamber and a sample analysis assembly received within the analysis chamber. The sample analysis assembly contains a carriage moveably supported within the analysis chamber and a sample container assembly mounted along the carriage and configured to receive at least one sample container containing a blood sample. The sample container assembly is linked to a drive mechanism for rotating the at least one sample container. The sample analysis assembly further contains a lighting assembly including a light array arranged adjacent to the sample container assembly in a position to direct light of a selected intensity towards at least one sample container. In an embodiment, the sample analysis assembly contains a camera supported along the carriage at a location inside the sample container assembly. This camera is configured to capture a plurality of images of the blood sample. In an embodiment, the movement of the carriage causes the sample container assembly and the camera to move together in a substantially coordinated motion. The motion of the carriage and rotating of the at least one sample container provides a complex motion to the blood sample therein. In an embodiment, the camera is a video camera that captures the plurality of images.

In an embodiment, the system can further include a mirror mounted along the carriage in a position to receive and reflect the plurality of images of the blood sample within the at least one sample container as the at least one sample container is transilluminated from above. The camera can be oriented or directed toward the mirror so that the camera receives the plurality of images of the blood sample reflected by the mirror. In an embodiment, the camera captures and records the plurality of images of the blood sample during certain intervals of each mixing cycle when a semi-opaque fluid within the sample container is sufficiently attenuated. In other embodiments, the camera can be directed at the at least one sample container, without the use of a mirror or other reflective surface for reflecting images of the at least one sample container. In an embodiment, the movement of the carriage causes the sample container assembly, a mirror, and the camera to move together in a substantially coordinated motion.

In an embodiment, the lighting assembly further includes at least one light shroud mounted in front of the light array and having a slit defined therealong. The at least one light shroud is movable so as to position its slit for directing the light from the light array toward a selected portion of the at least one sample container. In an embodiment, the light array of the lighting assembly includes a series of light emitting diodes and at least one driver for controlling the intensity of the light supplied by the light emitting diodes. In an embodiment, the light emitting diodes include a series of different color light emitting diodes configured to apply one or more different colors of light to the at least one sample container. In an embodiment, the light emitting diodes include a series of light emitting diodes configured to apply one or more different wavelengths of light to the at least one sample container. In an embodiment, the sample container assembly further includes a series of disks arranged to engage the sample container at spaced locations therealong. The disks provide a reduced profile and are linked to the drive mechanism to drive the rotation of the sample container.

In an embodiment, the carriage includes (a) a platform moveably mounted within and extending along the analysis chamber, (b) a series of upstanding supports configured to support the camera, the sample container assembly, and the light array, and (c) an agitation mechanism linked to the platform and configured to impart a lateral rocking motion to the carriage and a longitudinal rocking motion to the at least one sample container.

In an embodiment, the sample analysis assembly contains a camera that is positioned apart from the sample container assembly. Here, the sample containers are well within the "depth of field" of the camera image. The camera is located sufficiently away from the sample containers, such that the camera captures the plurality of images for analysis although the camera is stationary and the sample container is moving one or more of a longitudinal rocking motion, lateral motion, or rotational motion in one or more directions. In an embodiment, the camera is mounted in a fixed location beneath the sample container assembly or in a fixed location that permits view of the sample container assembly through a mirror. The camera is so equipped by means of an automatic focus mechanism to maintain focus upon the lower portions of the sample containers.

In an embodiment, an image analysis system for determining platelet function and coagulation status of an individual contains a frame delivering an analysis chamber and a sample analysis assembly received within the analysis chamber. The sample analysis assembly contains (a) a carriage moveably supported within the analysis chamber, (b) a sample container assembly mounted along the carriage and configured to receive at least one sample container containing a whole blood sample from the individual; and also linked to a drive mechanism for rotating the at least one sample container, (c) a lighting assembly including a light array arranged adjacent the sample container assembly in a position to direct light of a selected intensity and wavelength toward the at least one sample container; (d) a camera supported along the carriage below the sample container assembly, which is configured to capture a plurality of images of the blood sample, and (e) a controller configured to process the plurality of images of the blood sample from the camera for identifying one or more endpoints of hemostasis occurring in the blood sample and determining hemostasis status of the individual in response to the identification of the one or more endpoints of hemostasis. The movement of the carriage causes at least the sample container assembly and camera to move together in a substantially coordinated motion, and wherein the motion of the carriage and rotating of the at least one sample container provides one or more of a longitudinal rocking motion, lateral motion, or rotational motion in one or more directions to the blood sample therein. In an embodiment, the image analysis further contains a mirror mounted along the carriage in a position to receive and reflect images of the blood sample within the at least one sample container, and the camera is spaced from the mirror and oriented to receive the images of the blood sample reflected by the mirror.

In still a further embodiment, a system for hemostatic analysis of whole blood samples is provided, including a frame defining an analysis chamber, and a sample analysis assembly received within the analysis chamber. The sample analysis assembly further includes a carriage moveably supported within the analysis chamber. A camera is mounted along one side or at one end of the carriage, and a sample container assembly configured to receive at least one sample container containing a blood sample is mounted along the carriage in a position spaced from the camera, with the camera generally being focused substantially directly at the at least one sample container for collection of images of the sample(s) being tested assembly without requiring the sample container assembly to be trans-illuminated above, and/or without the use of a mirror or reflective surface to reflect images of the images of the sample(s) for collection by the camera. The camera will include a video camera or other camera capable of capturing and/or recording high-speed images of the at least one sample container, and include a shroud or cover over its lens for protection from dust or other airborne particles. The interior of the analysis chamber further generally will be substantially sealed to reduce dust or other airborne particles that could come into contact with the lens of the camera.

According to further aspects or embodiments, the sample container assembly can include a cartridge or cassette that is received within a supporting framework, and which includes one or more recesses within which one or more sample containers are received, with each sample container arranged in a substantially horizontally extending alignment with respect to the camera lens. The sample container can include at least one sample tube ranging from about 20 millimeters (mm) to about 90 mm in length and approximately 6 mm to 12 mm in diameter. The cartridge or cassette engages with a drive mechanism including a drive motor having a drive shaft that engages and drives a drive gear. This drive gear in turn engages gear teeth formed about a cap applied to each sample container. The drive mechanism imparts a rotational movement of the one or more sample containers within their cartridge. As the one or more sample containers are rotated, a vibratory or oscillating motion is imparted to the carriage of the sample analysis assembly by an agitation. The oscillating movement of the carriage is conveyed to both the sample container assembly and to the camera such that the camera is able to substantially move with and track the oscillating or vibratory movement of the sample assembly to help maintain focus of the images captured by the camera.

In addition, a lighting assembly, which can include a light array comprising a series of LEDs or other lights that can be selectively controlled is mounted on the carriage, adjacent the sample container assembly and on an opposite side thereof from the camera. The light array of the lighting assembly will be controlled by a system controller for the sample analysis assembly, for example to provide different intensities or different colors of lights directed at the sample tubes. In some embodiments, one or more movable light shrouds, each including an adjustable body having a directional slit formed along a distal thereof are moveably mounted within a cover positioned over the lights of the lighting assembly. The position and direction of the slits with respect to the lights and at least one sample container can be adjusted to focus and substantially control the amount and direction of light transmitted therethrough, so that the light generated by the lighting assembly can be substantially focused or restricted to a selected or desired area of the at least one sample container. As a result, the light will strike and shine through the sample, without shining directly into the lens of the camera or otherwise impairing the accuracy of the images captured by the camera. In embodiments, as the sample container is rotated, the light from the lighting assembly can be focused and directed from the side of the sample container so as to eliminate portions of the sample container where a standing wave in the fluid brings about the clumping of platelets, the precipitation of other matter from the solution or suspension, or combination of both. These precipitated matter or platelet clumps separate from the fluid within the sample container.

In some embodiments of the systems and methods for hemostatic analysis of whole blood samples according to the principles of the present disclosure, a system or analyzer controller is provided, including a program for controlling the operative components or elements of the hemostatic analysis system. For example, the system or analyzer controller can include programming to control the operation of the camera for collection of images of illuminated samples within the at least one sample container, and for performing analysis of the images to determine soluble fibrin precipitates as well as other, similar analyses or testing operations, including detections of irregularities in blood samples caused by viruses and other infectious agents, and other applications. In an embodiment, the virus is a severe acute respiratory syndrome coronavirus 2 (SARS-CoV-2). In embodiments, the system or analyzer controller generally will include a memory and can be linked, either directly or by a wireless modem or other communication device, to one or more servers, additional memory, and/or various other information handling systems of devices for transmission, analysis and/or storage of collected data/images and results of various testing/analyses conducted, e.g. for storage and/or transmission of hemostasis data. In further embodiments, the system or analyzer controller also can include machine learning programming, including development of a machine learning model, for enabling the controller to learn and update its analysis of received images. The system or analyzer controller further will communicate with a user interface or other user input/display through which the operator or user can input or set parameters for the analysis and/or collection of data based on the samples being tested and view results.

In an embodiment, the system or analyzer controller can initiate a sample analysis operation by the system for hemostatic analysis of whole blood samples, initiating the rolling/rotating motion or the sample containers and additional oscillating motion of the carriage, and recording and receiving images of the at least one sample container as collected by the camera. Using the recorded images, the system or analyzer controller can determine a first measurement of soluble fibrin levels of the subject samples under analysis, i.e. recording a first set of data points for the samples being tested at a first time (such as a start of the sample test, or when an indication of platelet clumping or other initial indicator(s) is detected). Thereafter, a second measurement of soluble fibrin levels can be received at a second time, with additional measurements of soluble fibrin levels being received/collected at later times up to detection/measurement of short chain (soluble) fibrin development within the sample(s). A set of estimated values of soluble fibrin at varying periods/times between the first and additional measurement times can be calculated and, together with data relating to the determined intervals for the hemostasis data based upon the detected hemostasis levels, input into a machine learning model. In some embodiments, the machine learning model can be further updated with review of historical data relating to the detection or sensing or formation of soluble fibrin or of platelet clumps in the samples.

Provided here are methods for evaluating a platelet aggregation property of a whole blood sample from an individual. One such method includes the steps of: (a) depositing a portion of the un-anticoagulated whole blood sample from the individual into a sample container; (b) subjecting the sample container containing the un-anticoagulated whole blood sample under specified temperature and reaction conditions to one or more of a longitudinal rocking motion, lateral motion, or rotational motion in one or more directions inside a system for analysis of the un-anticoagulated whole blood sample; (c) capturing images of the portion of the un-anticoagulated whole blood sample in the sample container until formation of platelet aggregates that are larger than 0.5 mm in diameter; (d) determining, based on the images, time elapsed from depositing the portion of the un-anticoagulated whole blood sample into the sample container to formation of the platelet aggregates; and (e) evaluating a platelet aggregation property of the blood sample in response to the elapsed time. The method can include the step of neutralizing chelating properties of citrate contained within an anticoagulated whole blood sample from the individual with a calcium solution to produce an un-anticoagulated whole blood sample. In an embodiment, the sample container is maintained at the specified temperature ranging from 25 to 40 degrees Celsius (° C.). In an embodiment, the sample container is maintained at the specified temperature of 37° C. In an embodiment, the sample container further contains diatomaceous earth, or kaolin, or combinations thereof. In an embodiment, the sample container further contains platelet agonists such as arachidonic acid, adenosine diphosphate, epinephrine, ristocetin, collagen and the like.

Provided here are methods for evaluating a platelet adhesion property of a whole blood sample from an individual. One such method includes the steps of: (a) depositing a portion of the un-anticoagulated whole blood sample from the individual into a sample container; (b) subjecting the sample container containing the portion of the un-anticoagulated whole blood sample under specified temperature and reaction conditions to one or more of a longitudinal rocking motion, lateral motion, or rotational motion in one or more directions inside a system for analysis of the un-anticoagulated whole blood sample; (c) capturing images of the portion of the un-anticoagulated whole blood sample in the sample container until platelet aggregates adhere to an inner wall of the sample container; (d) determining, based on the images, time elapsed from depositing the portion of the un-anticoagulated whole blood sample into the sample container to adhesion of platelet aggregates to the inner wall of the sample container; and (e) evaluating the platelet adhesion property of the blood sample in response to the elapsed time. The method can include the step of neutralizing chelating properties of citrate contained within an anticoagulated whole blood sample from the individual with a calcium solution to produce an un-anticoagulated whole blood sample. In an embodiment, the sample container is maintained at the specified temperature ranging from 25 to 40° C. In an embodiment, the sample container is maintained at the specified temperature of 37° C. In an embodiment, the sample container further contains diatomaceous earth, or kaolin, or combinations thereof. In an embodiment, the sample container further contains platelet agonists such as arachidonic acid, adenosine diphosphate, epinephrine, ristocetin, collagen and the like.

Provided here are methods for evaluating the quantity of soluble fibrin in a whole blood sample from an individual. One such method includes the steps of: (a) treating the whole blood sample from the individual with a citrate solution to produce a citrated whole blood sample; (b) depositing a portion of the citrated whole blood sample into a sample container with a reagent that contains a positively charged molecule that serves to precipitate the soluble fibrin; (c) subjecting the sample container containing the portion of the whole blood sample under specified temperature and reaction conditions to one or more of a longitudinal rocking motion, lateral motion, or rotational motion in one or more directions inside a system for analysis of the whole blood sample; (d) capturing images of the portion of the whole blood sample in the sample container until the soluble fibrin precipitates; (e) determining, based on the images, time elapsed from depositing the portion of the citrated whole blood sample into the sample container to the formation of a soluble fibrin precipitate; and (e) measuring soluble fibrin content of the blood sample in response to the elapsed time. The positively charged molecule can be a biological protein such as protamine, or a natural or synthetic positively charged polymer such as polybrene. In an embodiment, the soluble fibrin content of the blood sample is measured as soluble fibrin units which are calculated as 700 divided by the time (measured as seconds) elapsed from depositing the portion of the citrated whole blood sample into the sample container to the formation of a soluble fibrin precipitate. The soluble fibrin precipitate can be defined by coarse reddish clumps in a central region of the sample container. The soluble fibrin precipitate can be defined by transparent gel fragments along the standing wave portion of the fluid sample.

Provided here are methods for evaluating a clotting property of a whole blood sample from an individual. One such method includes the steps of (a) neutralizing chelating properties of citrate contained within an anticoagulated whole blood sample from the individual with a calcium solution to produce a diluted, un-anticoagulated whole blood sample; (b) depositing a portion of the un-anticoagulated whole blood sample into a sample container that contains a plurality of glass beads; (c) subjecting the sample container with the portion of the un-anticoagulated whole blood sample under specified temperature and reaction conditions to one or more of a longitudinal motion, lateral motion, or rotational motion in one or more directions inside a system for analysis of the whole blood sample; (d) capturing images of the portion of the un-anticoagulated whole blood sample in the sample container until the plurality of glass beads are entangled within fibrin strands; (e) determining, based on the images that have been retained, the time elapsed from depositing the portion of the un-anticoagulated whole blood sample into the sample container to the entanglement of the plurality of glass beads within fibrin strands; and (f) measuring clotting property of the blood sample in response to the elapsed time. In an embodiment, the method includes eliminating the images that are suboptimal because they are acquired during the portions of the rocking and rotating cycle when the layer of diluted whole blood is not sufficiently attenuated.

Another method for evaluating a clotting property of a whole blood sample from an individual includes the steps of: (a) neutralizing chelating properties of citrate contained within an anticoagulated whole blood sample from the individual with a calcium solution to produce a diluted un-anticoagulated whole blood sample; (b) depositing a portion of the un-anticoagulated whole blood sample with an added disclosure reagent such as Celite® or kaolin into a sample container; (c) subjecting the sample container with the portion of the un-anticoagulated whole blood sample under specified temperature and reaction conditions to one or more of a longitudinal motion, lateral motion, or rotational motion in one or more directions inside a system for analysis of the whole blood sample; (d) capturing images of the portion of the un-anticoagulated whole blood sample in the sample container until the characteristics of the fluid motion within the sample indicate the deposition of fibrin strands on the inner wall of the sample container has occurred; (e) determining, based on the images, time elapsed from depositing the portion of the un-anticoagulated whole blood sample into the sample container to the deposition of fibrin strands on the inner wall of the sample container; and (f) measuring clotting property of the blood sample in response to the elapsed time.

Another method for evaluating a clotting property of a whole blood sample from an individual includes the steps of: (a) treating the whole blood sample from the individual with a calcium solution to produce an un-anticoagulated whole blood sample; (b) depositing a portion of the un-anticoagulated whole blood sample into a sample container; (c) subjecting the sample container with the portion of the un-anticoagulated whole blood sample under specified temperature and reaction conditions to one or more of a longitudinal rocking motion, lateral motion, or rotational motion in one or more directions inside a system for analysis of the whole blood sample; (d) capturing images of the portion of the un-anticoagulated whole blood sample in the sample container until a three-dimensional spiral of platelet aggregates trapped in polymerized fibrin strands is formed; (e) determining, based on the images, time elapsed from depositing the portion of the un-anticoagulated whole blood sample into the sample container to formation of the three-dimensional spiral of platelet aggregates trapped in polymerized fibrin strands; and (f) measuring clotting property of the whole blood sample in response to the elapsed time.

Various objects, features and advantages of the present invention will become apparent to those skilled in the art upon a review of the following detailed description, when taken in conjunction with the accompanying drawings.

Figure 1A:
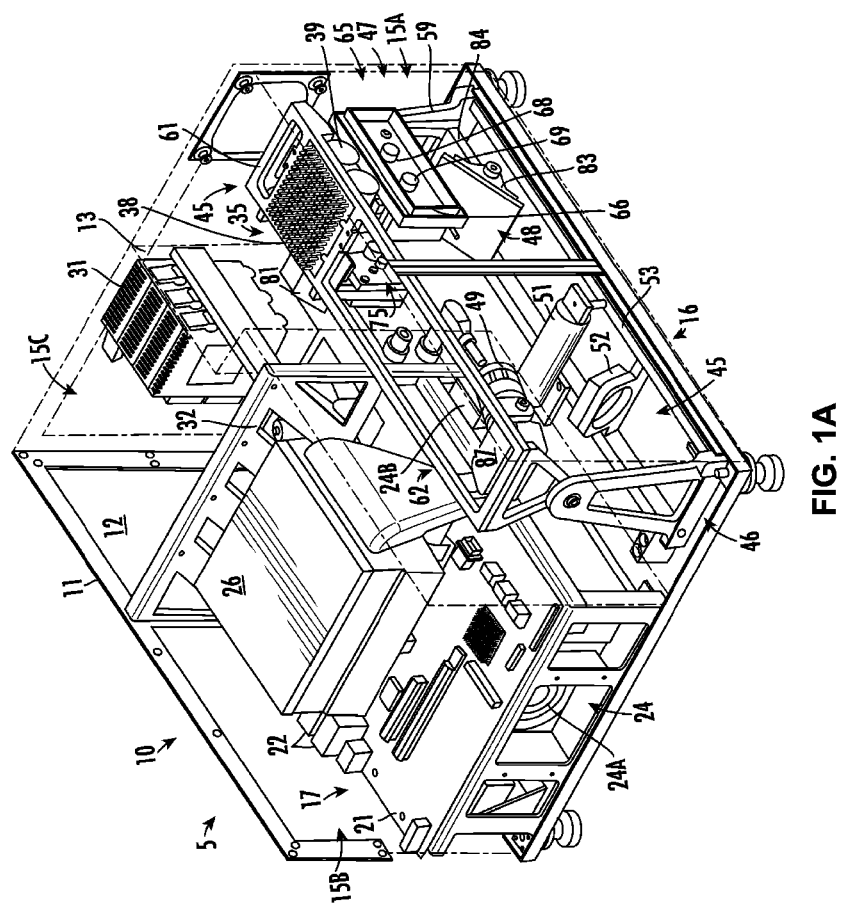
FIG. 1A is a perspective view of a system for platelet function and coagulation analysis according to one embodiment of the present disclosure.

Those skilled in the art will appreciate and understand that, according to common practice, the various features of the drawings discussed below are not necessarily drawn to scale, and that the dimensions of various features and elements of the drawings may be expanded and/or reduced to more clearly illustrate the embodiments of the present invention as described herein.

DETAILED DESCRIPTION

Described here are systems, reagent kits, and methods for concurrent assessment of both platelet function and coagulation as they interact during hemostasis. Disclosed here are systems and methods for analysis of whole blood samples to determine platelet function and coagulation competency in a substantially non-invasive, automated and efficient matter, and without necessarily requiring specialized training for operation thereof. In an embodiment, the systems and methods provide for a point-of-care testing for platelet function and coagulation properties of whole blood samples.

In one embodiment, the system for platelet function and coagulation analysis includes an analyzer or test unit including a frame defining a housing having a series of chambers therein. In an aspect, the housing is made of stainless steel. In one aspect, the platelet function and coagulation analyzer can have multiple chambers, including a chamber with a controller or motherboard for control of the operative assemblies of the analyzer and for image capturing and recording and analysis of the changes taking place in the sample tubes, a chamber with a lighting control mechanism including a series of drivers for controlling operation of a lighting assembly, and a sample analysis chamber in which a sample analysis assembly can be received and operated. Each of the chambers can be substantially isolated from one another or overlap with one another to form a continuous unit. The housing can include access doors to the various chambers for internal servicing in the event of a clean-up after a spill or for routine maintenance.

In one aspect, the controller or motherboard can include one or more processors having programming for controlling the various operative elements of the sample analysis assembly, including controlling the drivers for the lighting control assembly and heating elements, controlling fans for temperature regulation, and controlling the rotating and longitudinal rocking drive mechanisms that impart both a complex mixing movement and periodic attenuation to the diluted whole blood sample so as allow for various analytical steps during a multistep testing operation. The controller further can include programming for monitoring, detecting, and determining endpoints or other aspects of hemostasis, such as platelet function and coagulation adequacy. For example, the controller can include programming for monitoring, detecting, and determining the elapsed time from the initiation of a test to the formation of platelet aggregates within the blood samples. In another example the controller can determine the elapsed time from the initiation of the test to the formation of platelet aggregates of sufficient size to adhere to the walls of the sample container. In another example, the controller can include programming for monitoring, detecting, and determining the elapsed time from the initiation of a test to the occurrence of clotting. The system can be used to conduct a quantitative assay indicative of the time required for development of a soluble fibrin precipitate within a patient's blood sample for determining potential ongoing clotting tendencies, or risk of thrombosis. The controller further can be linked to a display or user interface through which an operator can initiate and control testing operations, view test results, or input parameters. The display also allows a user to control operation of the lighting assembly. The intensity and wavelength of light employed for detection can be varied to permit the optimal detection of the platelet function and coagulation endpoints. The controller further can be linked to a display or user interface through which decision support can be provided to a medical professional to assist with diagnosis or choice of therapeutic regimens. In an aspect, the display or user interface is an adjustable angle touchscreen.

The sample analysis assembly, in one aspect, generally can include a carriage moveably mounted within the sample analysis chamber, and which supports and imparts a coordinated rotating and longitudinal rocking motion to each of the various operative components of the sample analysis assembly. Such operative components of the sample analysis assembly can include a camera, a mirror, a sample container assembly, one or more heating element(s), one or more fans, and the lighting assembly. The carriage further can be mounted on or linked to an agitation mechanism so that the carriage can be moved in a desired longitudinal rocking or lateral motion or rotational motion or all three motions simultaneously in one or more directions to cause the blood sample under analysis to move in an ellipsoidal manner across the lower part of the short dimension of a test tube during testing. By supporting the various operative components of the analysis assembly on the moveable carriage, the movement of the operative components of the sample analysis assembly generally will be substantially matched or otherwise coordinated, for example, to help ensure the camera maintains focus and captures a clear set or stream of images of the samples during a sample analysis or test operation by providing a substantially consistent motion to each of the operative components moving in unison. In another embodiment, the camera can be equipped to capture a clear set or stream of images by equipping it with an auto-focus mechanism to compensate for an arrangement in which the camera is fixed and the sample container assembly is in motion.

In an embodiment, the sample analysis assembly maintains a relatively static spatial relation between the various components. The camera and the sample container assembly are in static spatial relation to each other while both the camera and the sample container assembly are individually subject to longitudinal rocking motion or lateral motion or both. The lighting assembly and the sample container assembly are in static spatial relation to each other while both the lighting assembly and the sample container assembly are individually subject to longitudinal rocking motion or lateral motion or both. The mirror and the sample container assembly are in static spatial relation to each other while both the mirror and the sample container assembly are individually subject to longitudinal rocking motion or lateral motion or both. Taken together, the sample analysis assembly maintains a static relationship among the camera, the lighting assembly, the mirror, and the sample container assembly. In an alternative aspect, the camera could be mounted in a position adjacent the sample container assembly with a substantially direct line-of-sight to the sample containers, and without the use of the mirror. For example, the camera can be mounted below the sample containers in place of the mirror and can be focused toward the sample containers to receive and capture images of the sample and record the formation of platelet aggregates in diluted whole blood along with coagulation of the blood samples therein.

In an embodiment, the sample analysis assembly maintains a moving spatial relation between the various components. The camera is in a static spatial relation, while the sample container assembly is subjected to both rotation and a linear rocking motion. The camera maintains a clear picture of events within the sample tubes by autofocusing on the fluid contained within the tubes or by adjustment of the length of the optical path so that the depth of field is sufficient to maintain the tube contents in sharp focus throughout the change in focal distance between the extremes of the rocking motion. The lighting assembly and the sample container assembly are in static spatial relation to each other while both the lighting assembly and the sample container assembly are individually subject to longitudinal rocking motion or lateral motion or both.

The sample container assembly generally can receive multiple sample containers, e.g., two or more disposable test tubes. The sample can be a reference sample or a whole blood sample from a patient or a control subject. The sample can be an extract from a whole blood sample from a patient or a control subject. The sample can be plasma from a whole blood sample from a patient or a control subject. In an embodiment, the sample occupies about one-fifteenth or less of the volume of the sample container. In an embodiment, the sample occupies about one-tenth or less of the volume of the sample container. In an embodiment, the sample occupies about one-fifth or less of the volume of the sample container. The sample containers will be received on a series of specimen container support rollers driven by a drive mechanism so as to cause rotation of the sample containers. The rotation of the sample containers, together with the longitudinal rocking motion or lateral motion provided by the carriage, imparts a controlled complex motion to the samples to help facilitate various aspects of platelet function and coagulation analysis, such as platelet aggregation and sticking of the platelet aggregates to the inner aspect of the sample containers, and coagulation and formation of fibrin precipitates. The controlled, complex motion induced in the samples induces a cycle in the fluid which both mixes the sample and cyclically attenuates the partially opaque fluid sample layer. This cyclical attenuation permits optical analysis of events occurring in the partially opaque fluid within the sample chamber.

In one aspect, the specimen container support rollers of the specimen container assembly can include a series of spaced disks, each with a reduced profile or thickness, and which provide support for the sample containers at spaced intervals therealong without substantially obscuring the camera's view of the samples within the sample containers. The specimen container support rollers further can include bands of frictional or engaging materials or surfaces extending about their circumference so as to engage and help drive rotation of the sample containers during a sample analysis operation.

The lighting assembly is located generally in a position relative to the sample containers such that light is directed through the sample containers. In an aspect, the lighting assembly generally is located in a position spaced above the sample containers and will direct light through the sample containers from above. In one aspect, light emitting diodes (LEDs) can be used to selectively emit varying wavelengths or intensities of light to the sample containers, with the selected wavelengths or intensities of such light generally being controlled by the controller. The light passes through the containers and an image of the blood samples therein will be directed to the carriage mirror positioned therebelow, or directly to the camera, i.e. in arrangements in which the camera is located below the sample containers or otherwise positioned in a substantially direct line-of-sight arrangement with respect to the sample containers. Adjustable and varied wavelengths of light are utilized to discern one or more endpoints of diagnostic significance in the blood specimen. For example, the lighting assembly is configured to provide an individual color of light (such as light of wavelengths corresponding to red, green, blue or white), or a combined use of multiple colors of lights to observe events of potential platelet function and coagulation significance in a blood specimen.

The carriage mirror, if present, can be oriented at varying positions or angles with respect to the sample containers and will receive and reflect the images of the samples within the sample containers toward the camera. The camera generally is arranged at an angle and location displaced from the carriage mirror at an opposite end of the sample analysis chamber, and its distance/position and tilt angle with respect to the carriage mirror can be adjusted to help provide an enhanced depth of field of the images of diagnostic interest.

In one aspect, the camera can include a video camera or other imaging device that can take high-speed video or images of the sample containers being reflected by the carriage mirror. In another aspect, the camera captures high-speed video or images of the sample containers directly. The video or images are transmitted from the camera to the controller which can perform image analysis, for example by analyzing selected frames or sequences of frames or pixels within the images, to detect platelet aggregates, short chain fibrin precipitates, and long chain fibrin polymers (coagulation). Upon detection of an endpoint of hemostasis, such as platelet aggregates of a defined size being formed within the sample containers, e.g., based on detection of a change in state of the images or a change in the quality and quantity of light passing through the sample containers due to the aggregation of the platelets or other aspects of coagulation within the samples inside the sample containers, the controller can determine that a certain endpoint of the clotting process has occurred, as well as the time to arrive at such endpoint. This information can be used to calculate potential risks of bleeding, of thrombosis or other potential issues. The video images can further be accumulated during the entire rocking cycle or they can be selectively acquired only during the time when the partially opaque fluid within the sample tube is attenuated, such that events occurring within it can be most easily and most clearly visualized. This latter approach significantly decreases the amount of information that must be processed in order to provide decision support to the medical professionals when they are called upon to confirm a questionable test result. As only snapshots of each complex-mixing and alternating thickening and attenuation of the layer of diluted blood process are captured by the camera to clearly record events occurring within the sample container, the camera/controller combination can produce a succinct version of events transpiring within the sample by assembling these snapshots into a video record for analysis.

FIGS. 1A-6F illustrate aspects of different embodiments of the systems and methods for platelet function and coagulation analysis of blood samples. In certain embodiment, the systems 5 or 100 for platelet function and coagulation analysis can receive and analyze samples of whole blood for clotting and coagulation endpoints or markers for the analysis and determination of time to arrive at those endpoints and potential risk factors of bleeding or thrombosis.

Figure 1B:
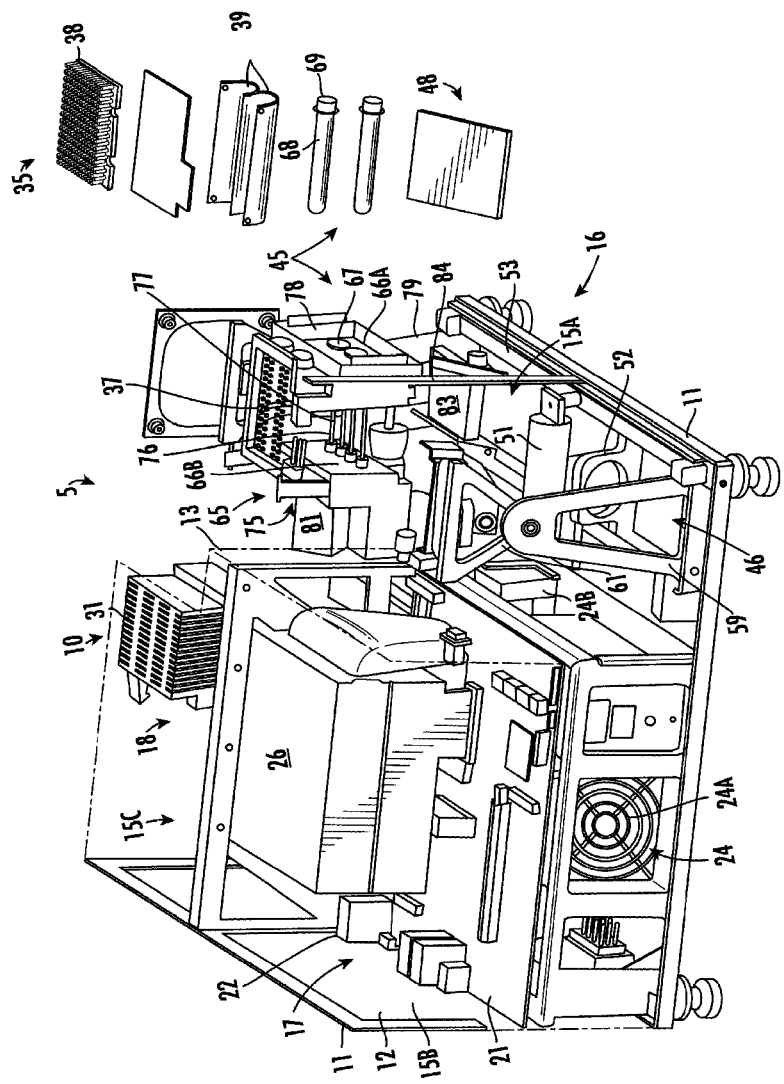
FIG. 1B is a further perspective illustration of the system for platelet function and coagulation analysis of FIG. 1A, with parts broken away to illustrate the sample container assembly.

As generally illustrated in FIGS. 1A and 1B, in one embodiment, the system for platelet function and coagulation analysis 5 can include a platelet function and coagulation analyzer 10 including a frame 11 with a series of outer panels 12 and internal walls 13 (FIGS. 1A-3B) defining an analyzer housing 14 having a series of internal chambers 15A-15C. The internal chambers 15A-15C can include a sample analysis chamber 15A, in which a sample analysis assembly 16 is located, and additional chambers 15B and 15C in which an analyzer controller 17 and a lighting control assembly 18 can be received, respectively. It also will be understood by those skilled in the art that fewer or additional chambers also can be provided. In addition, the outer panels 12 and/or interior walls 13 of the platelet function and coagulation analyzer 10 can be made removable for access to the interior of the internal chambers 15A-15C defined therein. The panels and walls also can be substantially secured to the frame 11 of the analyzer housing so as to substantially isolate the interior environments of each of the chambers as needed. For example, the chamber 15C enclosing the lighting assembly controls can be substantially sealed and/or insulated from the sample analysis chamber 15A to prevent excess heat from the lighting assembly controls entering the sample analysis chamber 15A.

As illustrated in FIGS. 1-3B, the analyzer controller 17 can include a motherboard 21 with a series of processors 22 or control modules that will include programming for controlling operation of the various operative assemblies of the platelet function and coagulation analyzer 10, including the sample analysis assembly 16 and the lighting control assembly 18. Similar or equivalent aspects are present in the system described in FIGS. 5A-5C. The controller also generally will include programming adapted to receive and analyze images of the blood samples during testing to measure and detect various markers or endpoints indicative of clotting of the patient's blood sample being tested. The controller further can include programming, modeling, and/or machine learning, that enable it to use the images of samples containing platelet aggregates or accumulations of fibrin to accurately detect similar occurrences in other samples and from the endpoints so detected to chart/graph time to formation of a clot, and for calculating potential risks of bleeding or thrombosis or other potential problems based on the detected endpoints/markers. In an embodiment, historical data is used for training the models. The controller will also include programming adapted to combine results from analyses of platelet function and coagulation spaced at several time intervals after withdrawal of blood from an individual's circulation. An individual can be a donor or a recipient of whole blood or blood products. From the combined results, the controller can conduct graphical analysis of both platelet function and coagulation and derive plots of the normal/abnormal physiology of these two components of hemostasis.

Figure 4:
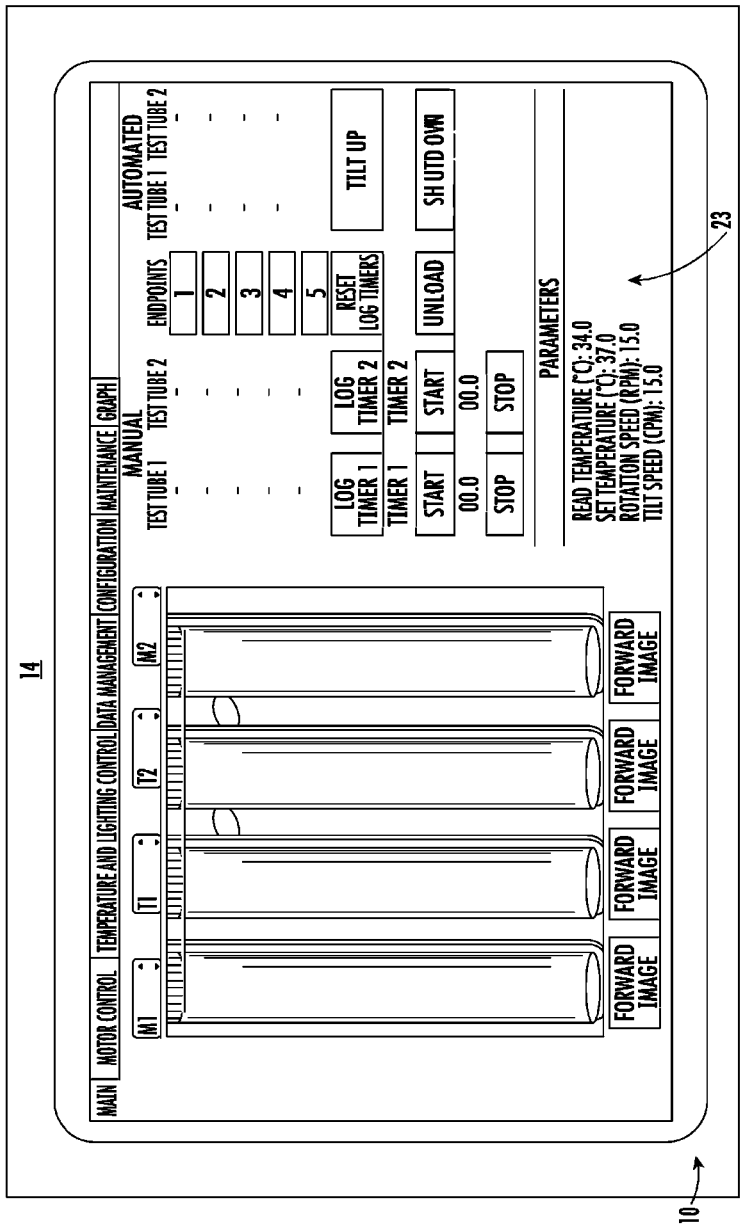
FIG. 4 illustrates an example embodiment of a user interface for the system for platelet function and coagulation analysis as illustrated in FIGS. 1A-3B.

As illustrated in FIG. 4, a user interface 23 can be provided along the housing 14 in communication with the analyzer controller to enable input and display of images of the samples and various parameters for control of various operative components of the platelet function and coagulation analyzer. For example, as illustrated in FIG. 4, in one embodiment, the user interface 23 can include a touchscreen with a series of tabs or on-screen buttons to enable the user to select between various operating screens such as for motor control, temperature and lighting control, data management, configuration, maintenance and graphing. Other control screens further can be provided and accessed as will be understood by those skilled in the art. The user interface also can include tabs or buttons for initiating a selected test routine as well as starting and stopping of tests, initiating or stopping a series of timers, as well as for adjustments, rotation, tilt, etc. of the blood sample containers. Those skilled in the art further will understand that additional user interfaces, such as a keyboard and mouse, etc., also can be used. The analyzer controller additionally can be linked to a server or other networked system or computer for transmission of the received data, images and calculated results as needed.

Figure 2:
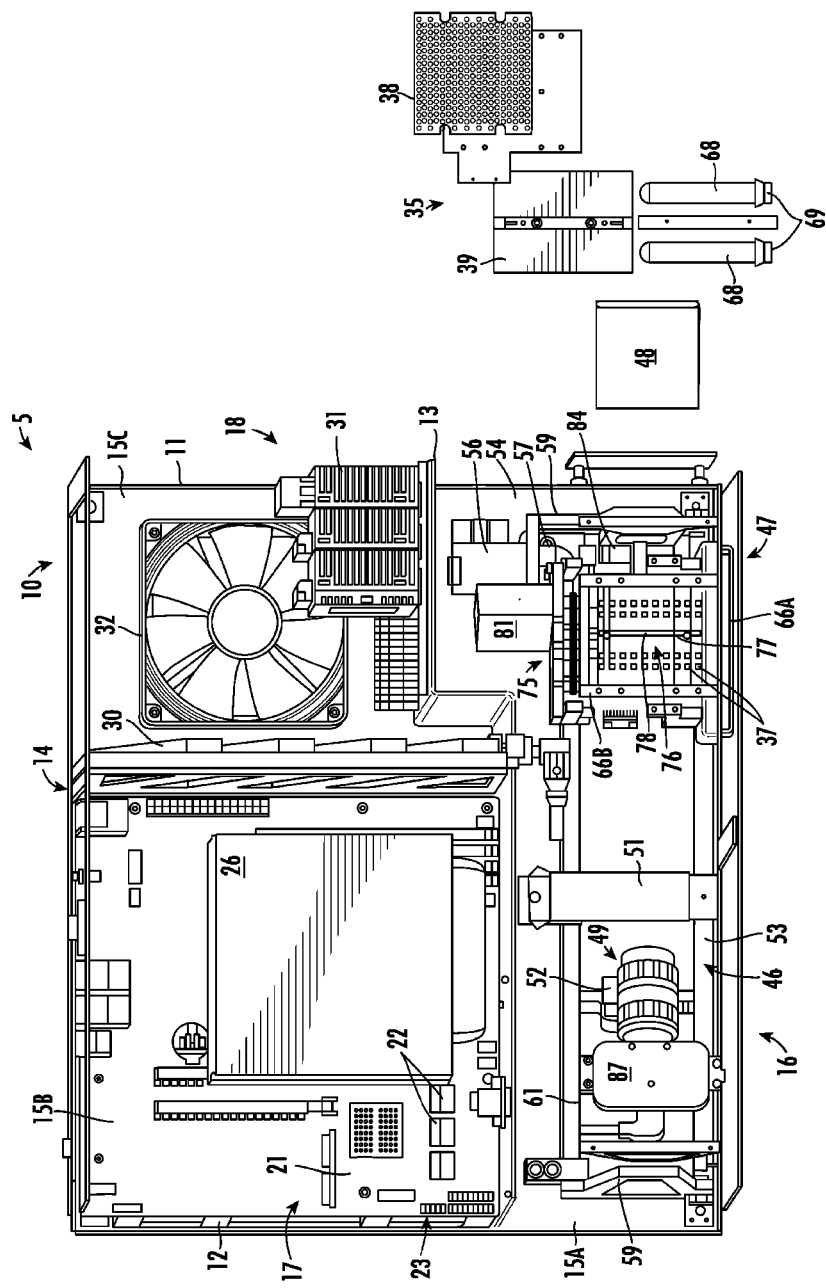
FIG. 2 is a further top plan view of the system for platelet function and coagulation analysis of FIGS. 1A-1B, with portions of the sample container assembly exploded.
Figure 3A:
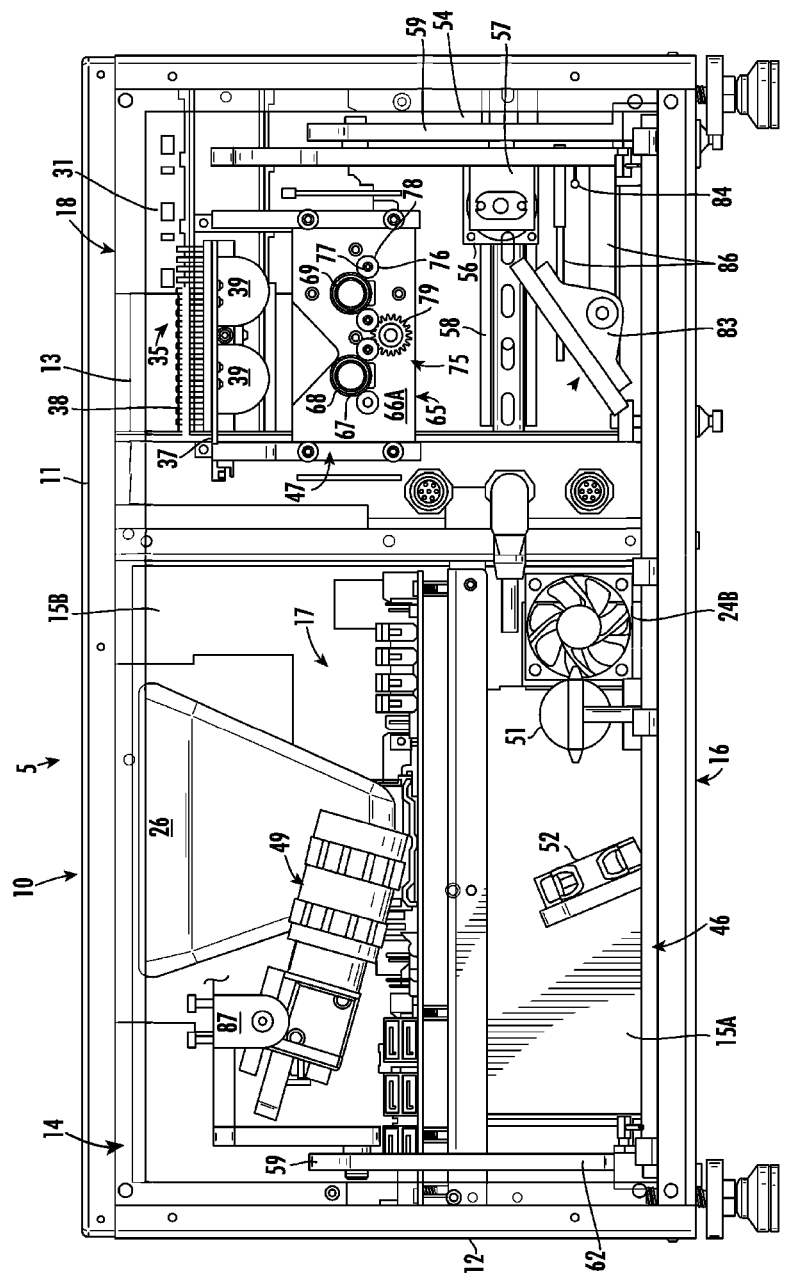
FIG. 3A is a side elevational view illustrating the analysis chamber of the system for platelet function and coagulation analysis according to an embodiment of the present disclosure.
Figure 3B:
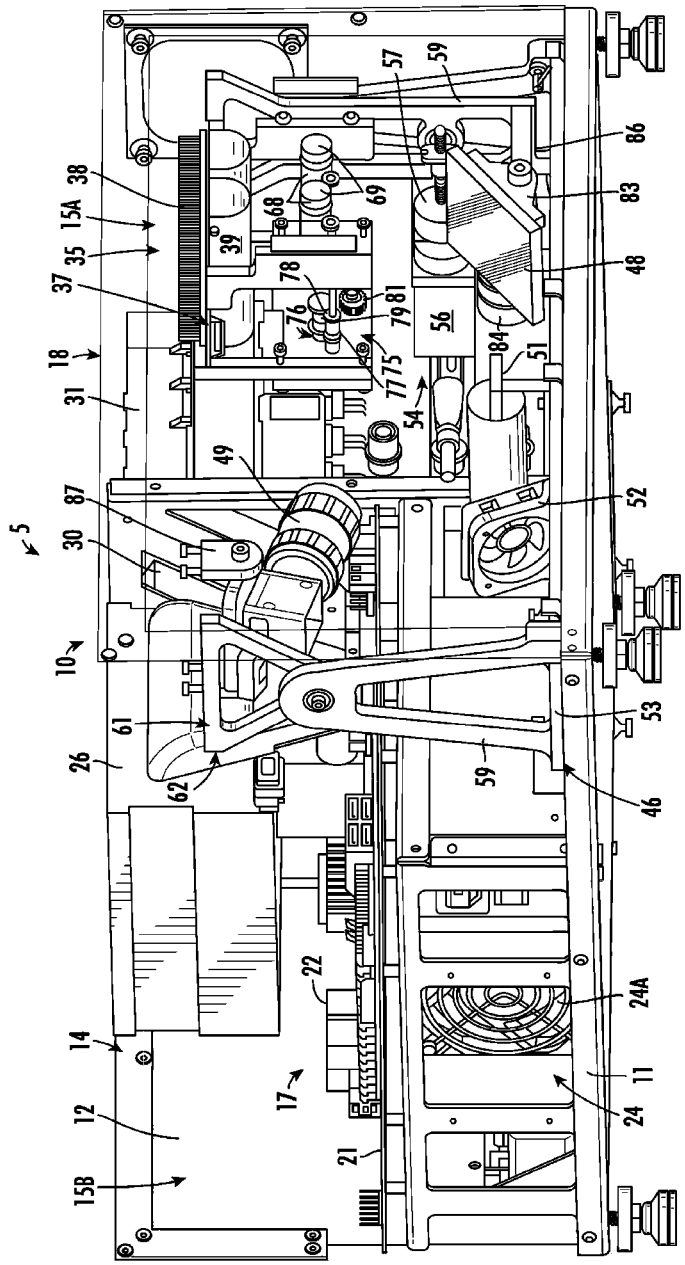
FIG. 3B is a perspective view of the system for platelet function and coagulation analysis of FIGS. 1A-3A.

One or more fans 24 (FIGS. 3A-3B) further can be provided within the chamber 15B housing the analyzer controller 17. This can include a first fan 24A for exhausting excess heat to the surrounding environment for the analyzer, and an additional fan 24B that can provide/direct additional heat from the chamber 15B housing the controller into the sample analysis chamber 15A as needed to help regulate and control the temperature therein to maintain the sample temperature at a desired level. Still further, a heat sink 26 can be provided, typically being mounted over the motherboard 21, as indicated in FIGS. 2, and 3A-3B. The heat sink 26 can be configured to draw heat away from the processors 22 mounted along the motherboard 21 to provide additional, passive cooling thereof. The heat sink can be provided with a fan to increase the effectiveness of heat removal. Similar or equivalent aspects are present in the system described in FIGS. 5A-5C.

FIGS. 3A-3B illustrate an embodiment of the lighting control assembly 18 received within chamber 15C of the platelet function and coagulation analyzer 10. In one embodiment, the lighting control assembly 18 can include a series of drivers 30 and a series of control modules 31 linked to a lighting assembly 35 that is located within the sample analysis chamber 15A. In addition, one or more fans 32 can be provided within the chamber 15C to help exhaust excess heat generated by the drivers 30 and control modules 31 outside of the housing of the platelet function and coagulation analyzer. Similar or equivalent aspects are present in the system described in FIGS. 5A-5C.

As further illustrated in FIGS. 2, 3A, and 3B, the lighting assembly 35 is received within the sample analysis chamber 15A, and can include a light array 36. In one embodiment, the light array 36 can include lights such as a series of light emitting diodes (LEDs) 37. The LEDs 37 further can include a series of different color LEDs (e.g., red, blue, green, white, etc.), that will be controlled by the lighting control assembly 18 to produce light of varying intensities and/or varying colors directed at the blood samples being tested. For example, blue light can be directed or applied to/against the blood samples to provide a contrast to the red color of the blood samples to help readily distinguish and identify the appearance of selected testing endpoints/markers. It will be understood that various types of lights also can be used, such as fluorescent lights or other light sources, and can be controlled to provide varying intensities of light directed toward and through the samples. Similar or equivalent aspects can be present in the system described in FIGS. 5A-5C.

A heat sink 38 can be mounted above and adjacent the light array 36 configured for passively removing heat generated by the operation of the lights of the light array to help control and maintain a desired temperature (i.e. approximately 37° C.) within the analysis chamber during testing. One or more diffusers 39 can be mounted in positions covering the lights of the light array 36 (as indicated in FIGS. 1A-1B and 2) for diffusing the light generated by the lights of the light array 36 and directed toward the blood samples being tested.

FIGS. 1A-1B, 2, and 3A illustrate an example embodiment of the sample analysis assembly 16 according to the principles of the present disclosure. In one aspect, the sample analysis assembly 16 will include a carriage 46 that supports the various operative components 45 of the sample analysis assembly 16. Such operative components 45 can include, among others, a sample container assembly 47, in which a series of sample containers 68 are received and rotated, a carriage mirror 48 (which may be adjustable), a camera 49, at least one heating element 51, at least one fan 52, and the lighting assembly 35. The carriage 46 further generally will be mounted to the frame 11 of the coagulation analyzer 10, for example.

In one embodiment, the carriage 46 can include a base frame or platform 53 that can be linked to a longitudinal rocking mechanism 54 (FIGS. 3A and 3B), which can include one or more motors 56 linked to the carriage 46 by a drive rod or coupling 57. In an embodiment, the track or guide rails 58 provide a base for the motor. In certain embodiments, the one or more motors 56 can be moved along the track or guide rails 58. In certain embodiments, the track or guide rails 58 can be linked to the carriage 46 that is moved by the one or more motors 56. The one or more motors 56 are operable under control of the analyzer controller 17 to cause a vibratory, longitudinal and/or lateral, back-and-forth and/or side-to-side motion of the carriage 46. Similar or equivalent aspects can be present in the system described in FIGS. 5A-5C.

As further illustrated in FIGS. 1A-1B and 3A-3B, the carriage 46 can include upstanding supports or legs 59 attached at their lower ends to the base frame or platform 53 of the carriage 46, and which are connected at their upper ends to an overhead or upper frame member 61. The carriage 46 thus defines a substantially unitary support structure 62 along which the camera 49, carriage mirror 48, lighting assembly 35 and sample container assembly 47 can be supported and statically linked together. Other operative components such as the heating element 51 and one or more fans also can be mounted or supported along the base frame or platform 53 as indicated in FIGS. 2 and 3A-3B. By mounting the various operative components 45 of the sample analysis assembly 16 along the carriage 46, the longitudinal rocking, vibratory or agitating movement of the carriage 46 is communicated or imparted to each of the operative components of the sample analysis assembly 16 so that the operative components 45 are moved together in a substantially coordinated, synchronized motion. Similar or equivalent aspects can be present in the system described in FIGS. 5A-5C.

As further illustrated in FIGS. 2 and 3A-2B, at least one heating element 51 will be mounted within the sample analysis chamber 15A, i.e., mounted to the base frame or platform 53. At least one fan 52 also can be mounted to the base frame or platform adjacent the at least one heating element. The heating element 51 will be controlled by the analyzer controller 17 to provide heat to the interior environment of the sample analysis chamber 15A, with the fan 52 likewise being controlled to provide an airflow across the heating element 51 to circulate and maintain the heated environment within the sample analysis chamber 15A at a selected temperature, for example, to maintain a test sample temperature of approximately 37° C. (i.e., at a temperature approximately equivalent to normal human body temperature). Additional variations in the temperature of the sample analysis chamber 15A, as regulated by the analyzer controller 17, also can be provided. Similar or equivalent aspects can be present in the system described in FIGS. 5A-5C.

The sample container assembly 47 generally will be mounted at one end of the sample analysis chamber 15A. As indicated in FIGS. 1B, 2, and 3A, the sample container assembly 47 can include a housing or support structure 65 with front and rear plates 66A/66B and open upper and lower portions. A pair of openings 67 can be provided in the front plate 66A for receipt of a pair of sample containers 68 therein. It will be understood by those skilled in the art that while a pair of sample containers 68 are illustrated for testing, additional or fewer sample containers also can be tested. Similar or equivalent aspects can be present in the system described in FIGS. 5A-5C.

The sample containers 68 can include disposable glass test tubes or other, similar tubes, and can be treated with a reagent compound that chelates or otherwise removes calcium ions from the blood sample and so delays initiation of hemostasis in the patient's blood samples being tested. The sample containers 68 can be received through the front plate 66A, each being inserted into one of the openings 67, and can be substantially sealed therein. For example, a sliding door or drawer face, can be provided along an outer panel of the analyzer housing to enable access to and insertion of the sample containers 68 into the sample container assembly. Springs or other biasing members also can engage end caps 69 at the ends of each of the sample containers 68 for urging and holding the sample containers 68 in an engaged position within the sample container assembly 47. These end caps 69 can further be utilized to impart rotary motion to the sample containers 68.

In an embodiment, a fast sample loading system is developed for a rapid test start. The sample containers 68 are directly inserted into the sample container assembly 47 that immediately engages the longitudinal rocking and rotating motion systems. In an embodiment, the sample containers 68 are loaded via an opening at the front of the coagulation analyzer 10, which enables ambidextrous use (right and left-handed laboratorians can use the machine).

The agitation assembly is designed so the entire assembly can be accessed through the housing doors and removed from the agitation and camera chamber as a single module. This enables the components (such as the camera, light system, etc.) to be easily accessed for cleaning or maintenance and allows any spills or dust within the device to be removed with ease.

In addition, the sample container assembly 47 includes a drive mechanism 75 operable under control of the analyzer controller 17 for rotating the sample containers 68. In one embodiment, the drive mechanism 75 can include a series of spaced sample container support rollers 76 mounted on sleeve bearings or ball-bearings and on which the sample containers 68 are received and supported, as indicated in FIGS. 2, 3A, and 3B. In one embodiment, the sample container support rollers 76 can be formed as a series of disks 77 mounted along spaced drive rods 78. Each of the disks 77 can have a reduced profile and/or thickness configured to provide sufficient support to each of the tubes at spaced locations along the lengths thereof, while further substantially minimizing the area or portions of the sample containers potentially obscured from view by the engagement of the sample containers 68 with the rollers. The tube supporting disks or support rollers also can include rubber gaskets 79 or other, similar materials, or can have roughened outer rim surfaces, configured help to provide an enhanced frictional grip between the rollers and the sample containers so that the rotation of the sample container support rollers 76 in turn causes the sample tubes, or cuvettes to be rotated. Similar or equivalent aspects can be present in the system described in FIGS. 5A-5C.

The sample container support rollers 76 can be rotated by a series of gears 81 or other, similar drive mechanism linked to a drive motor 82 (FIGS. 3A and 3B). The drive motor 82 will be operated under control of the analyzer controller 17, and will control the rotation of the sample containers 68 based on programmed parameters that can be input via the user interface 23 as indicated in FIGS. 4 and 5D, to rotate the cuvettes/sample containers 68 at a predetermined or substantially consistent rotational rate. Rotation of the sample containers 68, combined with the oscillating, longitudinal rocking and/or vibratory motion imparted to the sample container assembly 47 by the motion of the carriage 46, creates a complex motion designed to facilitate platelet aggregation and/or platelet adhesion to the inner aspect of the sample container while simultaneously facilitating coagulation of the blood samples by providing a phospholipid catalytic surface within the sample containers 68. Similar or equivalent aspects can be present in the system described in FIGS. 5A-5C.

In addition, as the sample containers 68 are rotated, light of a selected intensity and/or color is directed from the LEDs (or other lights) of the lighting assembly 35 (FIG. 2) will be directed toward/through the tubes. As further illustrated in FIGS. 3A and 3B, the carriage mirror 48 generally will be mounted below the sample container assembly 47, in a position to receive and reflect images of the sample containers 68 as the sample containers 68 are rotated and the light from the lighting assembly 35 is directed through or applied thereto. The carriage mirror 48 can be adjustable both longitudinally and laterally and the tilt angle of the carriage mirror 48 with respect to the sample containers 68 further can be adjusted or varied. For example, the carriage mirror 48 can be mounted on a pivoting support 83 and linked to a motor or actuator 84 by adjustment rods 86. The positioning and tilt angle of the carriage mirror 48 can be input via the user interface as indicated in FIGS. 4 and 5D and the analyzer controller 17 can engage the actuator 84 to adjust the mirror.

As the light passes through the sample containers 68, images of the sample containers 68 are collected and reflected toward an opposite end of the sample analysis chamber 15A by the carriage mirror 48. The reflected images will be picked up by the camera 49, which generally is mounted at a location downstream from the carriage mirror 48 and the sample container assembly 47, as indicated in FIGS. 1A and 3B. The camera 49 can include a multi-megapixel camera or a video camera or other high-speed image capture system. The camera 49 further generally will be adjustably mounted along the upper frame member 61 of the carriage framework by a clevis or bracket 87, enabling adjustment of the camera tilt angle and its position laterally, longitudinally, and vertically with respect to the carriage mirror 48. The camera 49 will be supported from the upper frame member 61 of the carriage 46, with the angle and positioning of the camera 49 with respect to the carriage mirror 48 being adjusted to enable focusing of a folded optical path of the images as reflected by the mirror to enhance a depth of field of the optical path for transmission to and receipt of the sample images by the camera 49. In another embodiment, the camera 49 may be supported from the lower frame of the carriage 46 or at any intermediate point with the mirror tilt adjusted so as to enable focusing of the camera 49 on the lower portion of the sample container tubes.

The camera will capture a series of video or high-speed images of the blood samples contained within the sample containers 68 as the sample containers 68 are rocked longitudinally, rotated and oscillated or vibrated, thus undergoing their complex motion, and will relay this information back to the analyzer controller 17. The analyzer controller 17 can analyze the images, for example, analyzing selected images of a series of incoming images (e.g., every other image of the stream of images being input or only those images where the blood sample contained within the sample container is sufficiently attenuated to allow for a clear image), and/or can further analyze images within such frames on a substantially pixel-by-pixel basis. Images will be analyzed to determine their starting and endpoint measurements of time for platelet function and coagulation of the blood samples contained within the sample containers 68. Based on such image analysis, starting and endpoints for platelet function and coagulation can be determined with increased precision, the images recorded during that part of the complex mixing and cyclical attenuation cycle that contain no useful information can be discarded and the time-compressed sequence of the remaining images further can be used for visual confirmation and for training the analyzer controller 17 for enabling enhanced detection of such endpoints and starting points.

In addition, the camera 49 could be located in a position so as to have a substantially direct line-of-sight view of the sample containers 68, without utilizing the mirror. For example, the camera 49 could be mounted below the sample container assembly 47 in place of the carriage mirror 48 and in this location, it would be configured to collect images of the sample containers 68 and the coagulation and platelet formation of the samples therein, without such images being reflected to the camera 49 via the mirror.

Figure 5A:
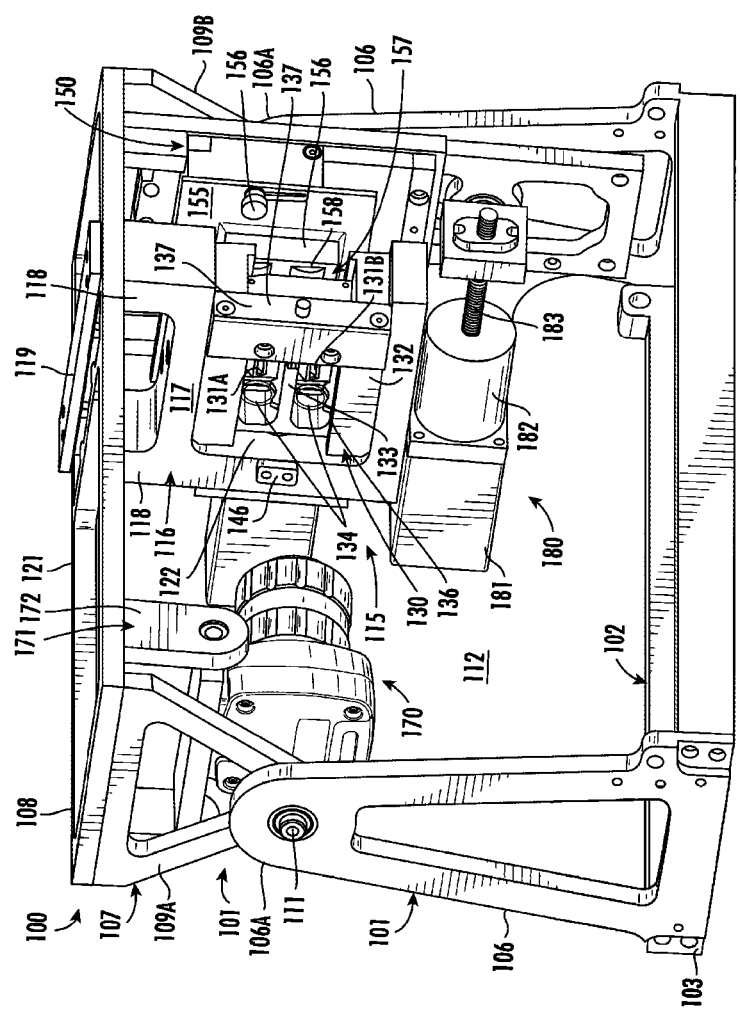
FIG. 5A is a perspective view of an additional embodiment of a system for platelet function and coagulation analysis according the principles of the present disclosure, with parts broken away for clarity of illustration.
Figure 5B:
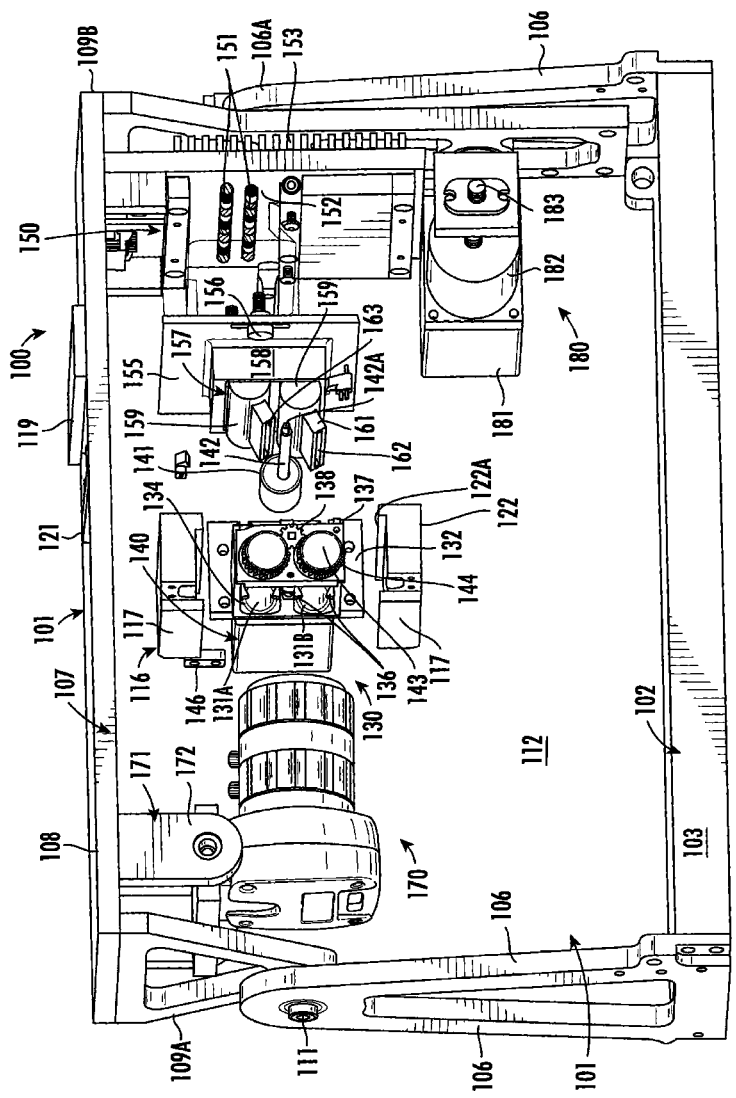
FIG. 5B is an exploded perspective view of the embodiment of a system for platelet function and coagulation analysis of FIG. 5A, illustrating components of a sample container assembly according to the principles of the present disclosure.
Figure 5C:
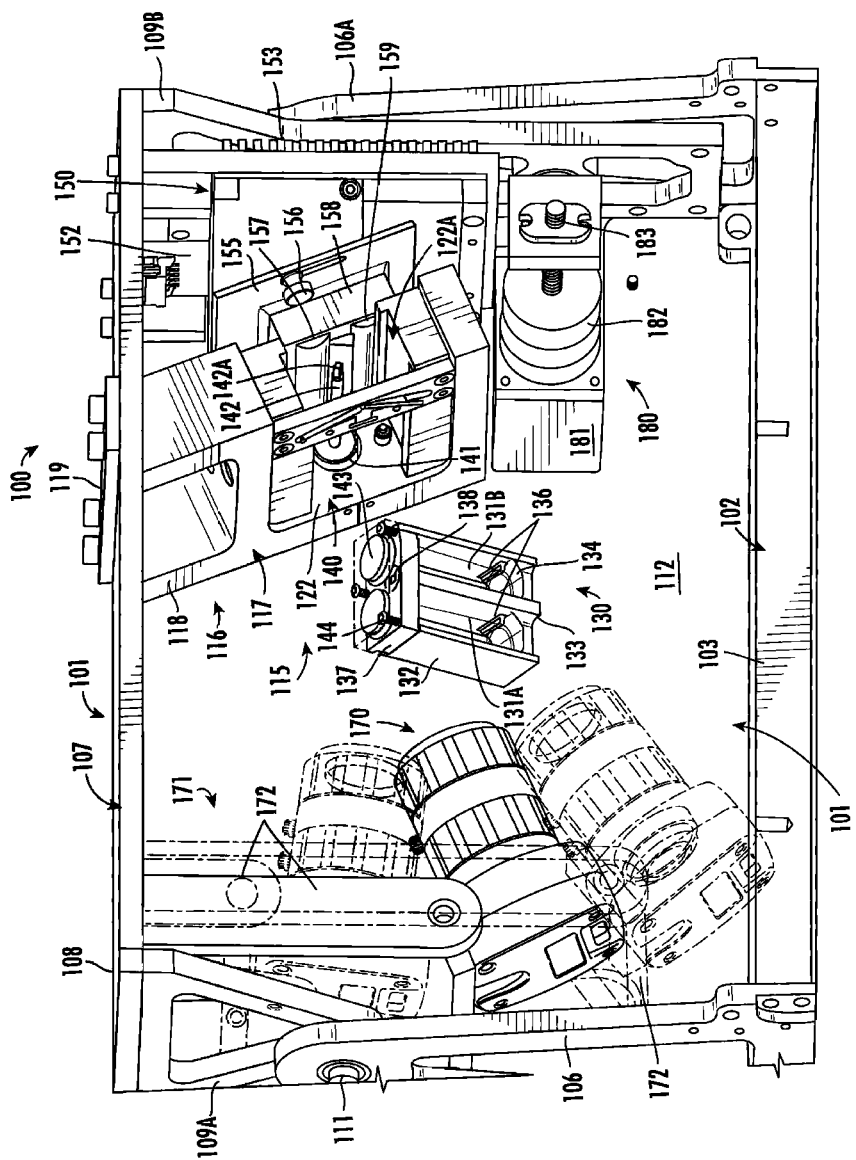
FIG. 5C is perspective view of the embodiment of a system for platelet function and coagulation analysis of FIGS. 5A-5B, illustrating varying camera positioning and with components of a sample container assembly according to the principles of the present disclosure broken out for illustration.
Figure 5D:
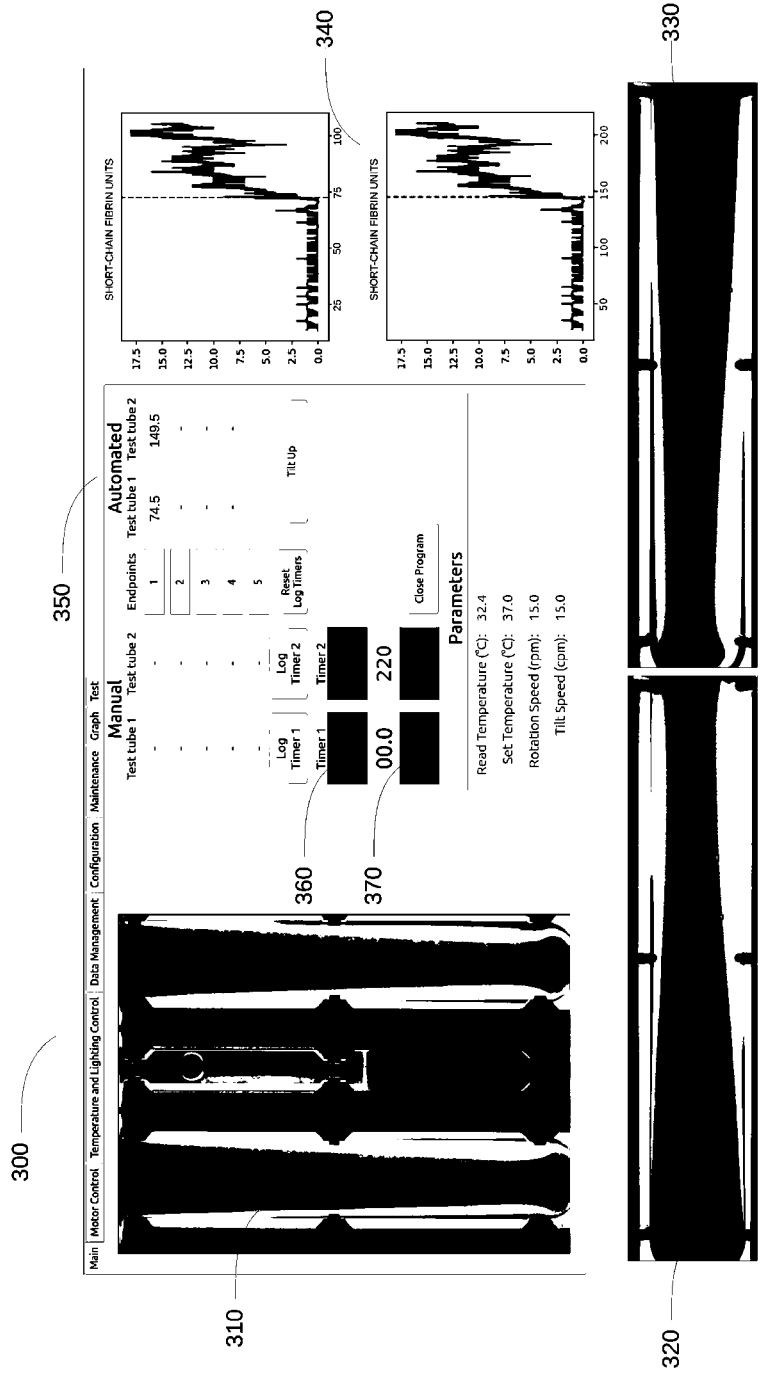
FIG. 5D illustrates an example user interface including display of example data as generated by a hemostasis analysis system as discussed herein, according to aspects of the disclosure.

An additional embodiment of a system 100 for hemostatic analysis of blood samples and/or for use in analysis of other bodily fluids, is illustrated in FIGS. 5A-5C. Though not shown in FIGS. 5A-5C, the system 100 for hemostatic analysis of blood samples illustrated in these FIGS. 5A-5C incorporates and includes a number of features or components illustrated in the embodiment(s) of FIGS. 1A-3B, but which components or features have, however, been omitted from FIGS. 5A-5C for purposes of clarity of illustration of the embodiment depicted therein. For example, the system for hemostatic analysis of blood samples 100 will include a system or analyzer controller, analyzer cabinet or enclosure, fans or other cooling devices, one or more heating devices, and other components as depicted above with regard to FIGS. 1A-3B.

As generally illustrated in FIGS. 5A-5C, the system for hemostatic analysis of blood samples 100 will comprise a sample analysis assembly 101 or test unit having a frame 102 with a base 103 and one or more upstanding supports or stanchions 106, and a cradle or carriage 107 movably mounted to the frame 102. For example, the carriage 107 or cradle of the sample analysis assembly 101 or test unit can include a body 108 or upper frame section with supporting yokes 109A and 109B that project downwardly therefrom at opposite ends of the body 108. The yokes 109A and 109B of the carriage will be pivotally, rotatably, or otherwise movably mounted to the upstanding ends 106A of the frame stanchions or supports 106, such as by bushings 111 or other, similar mechanisms so as to enable a rocking, oscillating or other motion of the carriage 107. In addition, sample analysis assembly 101 generally will include a cabinet or enclosure (not shown) mounted to the frame 102 and defining an analysis chamber 112, which analysis chamber 112 generally will be substantially sealed from the external environment to prevent ingress of dust and other particulate matter into the chamber, as well as to facilitate control of the temperature therein as needed to help maintain the samples being tested at a selected or desired or temperature for the testing being conducted.

As further illustrated in FIG. 5A, the sample analysis assembly 101 includes a sample container assembly 115 mounted on a support structure 116 that is mounted to and extends downwardly from the upper frame portion or body 108 of the carriage 107. The sample container assembly support structure 116 can be adjustable or movable along the body 108 of the carriage 107, and can be secured in place using fasteners, and will be configured to receive a cartridge 130 or cassette containing one or more sample containers 131A/131B. For example, as illustrated in FIGS. 5A and 5C, the sample container assembly support structure 116 can include a body 117 having one or more supporting arms or portions 118 that can be affixed to a slidable or adjustable mounting plate 119, which can be mounted to the upper surface 121 of the carriage body by a series of fasteners that can be removed or otherwise sufficiently disengaged to facilitate movement of the support structure 116, and the sample container assembly 115 with it, along the carriage body. As indicated in FIG. 5C, in some embodiments, the support structure also can be pivotable as needed or desired to orient or arrange the sample containers 131A/131B within the analysis chamber 112. The body of the support structure further can include a substantially U or C shaped recess or cavity 122 defined therein, and within which the sample container cassette or cartridge 130 containing the one or more sample containers 131A/131B will be received. In addition, the open end 122A of the cavity 122 can be sealed and unsealed via a door or other access panel (not shown) along the cabinet of the sample analysis assembly for insertion and removal of the sample container cartridge or cassette, as discussed above with respect to the embodiment(s) of FIGS. 1-3B. The analysis chamber thus can remain substantially sealed, while the cassette or cartridge containing the sample containers can be slidably inserted and removed from the support structure of the sample analysis assembly or test unit for testing.

In an embodiment, the sample container assembly contains upper and lower supports defining recesses in which a sample container is received, and a drive mechanism including a drive motor coupled to a drive gear. As the drive gear is rotated by the drive motor, the drive gear engages geared portions of the sample container to drive rotation of the sample container. As further illustrated in FIGS. 5B and 5C, the sample container cassette or cartridge 130 will include a body 132 with a central wall 133 defining one or more (i.e. two) container receiving recesses or chambers 134, each sized and/or configured to receive a sample container 131A or 131B of a desired or selected size. For example, while the sample container cassette or cartridge is shown in FIGS. 5A-5C with two sample containers received therein, it will be understood by those skilled in the art that variations, including cassettes or cartridges with one recess for receiving a single sample container, or more than two recesses for receiving more than two sample containers, also can be utilized. The sample container cassette or cartridge 130 further can include tabs or supporting projections 136 at one or both ends of the container receiving recesses 134, which tabs, and the body 132 of the sample container cassette or cartridge 130 further typically will be made from a polymer or plastic material having a low coefficient of friction such that the sample containers can easily rotate while resting thereon, without requiring additional bearings or other rotating supports to be provided within the recesses or chambers.

A front plate 137 is fitted over and secured to the body 132 of the sample container, cassette or cartridge, such as by a series of removable fasteners, as indicated in FIGS. 5B and 5C. Note that in FIG. 5C, the sample container cassette or cartridge is turned for illustration. In addition, the central wall 133 of the body of the sample container cartridge or cassette can include a passage extending therethrough and terminating at a first or forward end within the front plate 137 and within which a drive gear 138 will be received.

As further illustrated in FIGS. 5A and 5B, a drive mechanism 140 is provided for rotating the sample containers 131A/131B with the sample container cassette or cartridge 130, generally being mounted to the sample container support structure. The drive mechanism 140 can include a variable speed, reversible servo motor or a similar drive motor 141 controlled by the analyzer or system controller for the system for hemostatic analysis of blood samples 100, and having a drive shaft 142 that is received in and projects along the passage formed through the central wall 133 of the sample container cassette or cartridge 130 when the sample container cassette or cartridge is received within the recess of the support structure 116. The forward or distal end 142A of the drive shaft 142 will engage the drive gear 138 mounted along or integrated within the front plate of the cartridge or cassette such that the drive gear is driven/rotated by the drive motor.

The sample containers 131A/131B can include glass or plastic sample tubes, and can include disposable or single use tubes. The sample container can include at least one sample tube ranging from about 20 mm to about 90 mm in length and approximately 6 mm to 12 mm in diameter. The sample container can range from about 20 mm to 70 mm in length or from 30 mm to 90 mm in length. In some embodiments, the sample container can include a disposable clear glass or plastic sample tube, having a length of between about 20 mm to 40 mm and a diameter of between about 6 mm to 8 mm. In some embodiments, the sample containers further can be of a reduced size, with a length of between approximately 20-30 mm to approximately 35-45 mm, and can have a diameter of approximately 6 to 12 mm. For example, the sample containers can include approximately 8 mm×30 mm clear glass or plastic tubes each sealed with a cap or enclosure 143 that will engage and/or bear against the front surface of the front plate of the cartridge or cassette when the tubes are inserted therein. The caps 143 also generally can include a series of gear teeth 144, or can include a separate gear or sprocket provided thereabout, which gear teeth 144 will be configured to engage the teeth of the drive gear 138 integrated into the front plate of the cassette or cartridge. As the drive motor drives rotation of the drive gear, the sample containers thus are likewise caused to be rotated by the engagement of the teeth of their caps with the drive gear.

As additionally shown in FIGS. 5A and 5B, a thermocouple 146 or other temperature probe or sensing device can be mounted to the sample container support structure for measuring and/or providing readings of the temperature within the analyzer chamber to the system or analyzer controller. Typically, the thermocouple or temperature probe will be mounted or positioned as close as possible to the sample containers although the position or mounting thereof can be varied as will be understood by those skilled in the art. Also, other sensors for reading other parameters or conditions also can be used.

As further illustrated in FIG. 5B, a lighting assembly 150 will be mounted or positioned behind the sample container assembly 115, generally mounted to and/or supported by the carriage body such that as the carriage is oscillated, swung or otherwise moved the lighting assembly 150 will be maintained in a substantially fixed attitude with respect to the sample container assembly 115. The lighting assembly 150 generally will include an array of lights 151, which can include a series of light emitting diodes (LEDs), although other types of lights also can be used, which will be controlled by the system or analyzer controller to produce and/or transmit light of different colors and/or intensities. The lights typically can be mounted to a circuit board 152, and will include a driver connected to the system or analyzer controller, with a heat sink 153 or other, similar cooling mechanism generally being provided along a back side of the lighting assembly 150 for removal of excess heat generated by the lights. Fans or other cooling devices (not shown) also can be included to help remove excess heat from the analysis chamber (not shown) also can be provided to heat/raise the temperature in the analysis chamber as needed to help maintain a substantially constant temperature for the analysis or testing being performed.

A cover 155 is slidably mounted over the light array 151, the position of the cover 155 being adjustable vertically with respect to the lights 151 of the lighting assembly 150, as such as by sliding movement of the cover along a front portion of the lighting assembly and affixing it in position via a set screw or other similar locking mechanism 156. One or more lighting shrouds 157 further can be received within a forwardly projecting portion 158 of the cover 155. Each of the lighting shrouds 157 generally include a body 159 that can be pivotally or rotatably mounted within the forwardly projecting portion 158 of the cover, and including a projection or forwardly extending portion 161 having a slot or slit 162 formed along the distal or front end 163 thereof. The lighting shrouds can be adjusted vertically and their slits can be adjusted/oriented at an angle with respect to the sample containers 131A/131B, so as to direct, and to an extent limit, the light transmitted from the lights 151 of the lighting assembly at or toward selected portions of the sample containers. For example, the slits can be arranged to focus and direct the light from the lights at portions of the sample containers where a standing wave will be created within the fluid in the sample containers. Clumps of platelets or other particulate matter are formed within the standing wave that is produced in the blood sample by the down-sweeping rotation of the sample container as it forces the contained fluid into ellipsoidal motion across the short dimension of the sample container. As a result, the light being emitted from the lighting assembly can be substantially restricted to illuminating or shining through the fluid contained within the sample containers, while avoiding shining of the light directly into the lens of the camera 170 capturing images of clotting and/or the formation or clumping of platelets in the blood samples being tested.

As indicated FIGS. 5A-5C, the camera 170 will be mounted at one end of the analysis chamber 112 opposite the sample container assembly 115 and lighting assembly, generally being substantially directly focused at the sample containers 131A, 131B received within the sample container assembly 115. In this embodiment, a mirror or other reflective surface for reflecting images of the sample tubes is not required, nor is it required for the sample containers 131A, 131B to be transilluminated from above. As a result, testing using this embodiment of a sample analysis assembly can be performed using sample containers 131A, 131B of a reduced size or configuration, without substantially impinging or restricting the ability of the camera 170 focus and to accurately capture images of the sample containers 131A, 131B during testing. The camera 170 generally can include a video camera or other high speed camera with the ability to take high resolution video and/or still images at a substantially rapid rate, and will be linked to or otherwise in communication with the system or analyzer controller so that the images collected by the camera 170 of the samples within the sample containers 131A, 131B are recorded thereby. As further illustrated in FIG. 5C, the camera 170 will be mounted to an adjustable camera support assembly 171 that can include one or more of a yoke, arm or gimbal mechanism 172 that is supported from the body 108 or carriage body. The adjustable camera support assembly 171 is adjustable/moveable in one or more directions, i.e., it can be adjustable vertically and along one or more axes so as to enable the position of the camera 170 to be adjusted vertically, at different heights in the analysis chamber 112, and enables adjustment of an angle or orientation of the camera 170 with respect to the sample containers 131A, 131B received within the sample container assembly 115, as indicated by the varying camera positions shown in FIG. 5C. In addition, a shroud or cover may be mounted over the camera lens to minimize or reduce collection or depositing of dust or other airborne particulates onto the lens of the camera 170.

Still further, an agitation mechanism 180, including a motor or other actuator 181 for creating agitation or oscillating movement of the carriage 107 can be mounted to the frame of the sample analysis assembly, for example along a lower end thereof as generally illustrated in FIGS. 5A-5C. The motor 181 can include a gear reducer or gear box 182 with a drive shaft 183 that extends into the analysis chamber 112 and is coupled to the distal or rear supporting yoke 109B of the carriage 107. As the motor 181 rotates its drive shaft 183, the carriage 107 can be caused to swing or oscillate with respect to the frame. Since the camera 170, lighting assembly, and sample container assembly 115 are all secured to the carriage 107, the oscillating motion of the carriage will be transmitted to each of the camera 170, sample container assembly 115, and lighting assembly so that these operative elements move together in a substantially coordinated motion. As a result, the camera 170 can substantially maintain its focus and tracking of the sample tubes as the sample tubes are both rotated and oscillated in an irregular motion or movement to provide substantially accurate capture and recording of images of the samples within the sample containers 131A, 131B during testing.

FIG. 5D depicts an example user interface 300 showing a platelet aggregation/adherence analysis as described herein. For example, in some embodiments the user interface 300 may be generated by user interface generator 235 as described below with reference to FIG. 6A. In an example, the user interface 300 may be a graphical user interface (GUI), web-based user interface, or web application The user interface 300, or variants thereof, may be displayed on a mobile device, a personal computer, a web browser, a smart watch, or other computing devices. The user interface 300 includes an interface allowing the performance and/or termination of a platelet aggregation/adherence assay or a coagulation assay or a soluble fibrin assay. In one embodiment, the user may record the assay with an optical system. Rather than an optical system, a different sensor or combination of sensors may be utilized in other embodiments of this system. Furthermore, an assessment of the hemostatic status of the individual may be provided. In some implementations, the optical system and/or other sensor(s) and/or software may pass data to the system or hemostasis analyzer controller to analyze and/or test additional hemostasis conditions and/or circumstances. Based on the platelet aggregation/adherence levels, a user interface generator 235 may generate additional user interface element(s) that provide hemostasis data and levels. In some embodiments, a user interface generator 235 may provide the platelet aggregation/adherence and/or other hemostasis levels regardless of their range.

In some embodiments, platelet aggregation/adherence phenomena may be observed and/or quantified in, or sourced (wholly or in part) from, a blood sample obtained directly from a living donor, while in other embodiments stored or partially-preserved whole blood may be used, and as discussed above, changes in state within the samples being tested are observed by visual detection. The visual observations/images of the samples further generally may be analyzed using the system or analyzer controller, which can include programming, instructions stored in memory or a machine-readable storage medium, or software and/or physical mechanisms for analysis of blood or other fluid samples. For example, FIGS. 6A-6D illustrate an embodiment of a system or analyzer controller, and methods of operation thereof, including the use, in some embodiments, of a machine learning model or module for assessing and updating the operational programming of the system or analyzer controller to improve its ability and/or accuracy of measurement and characterization of the detection/determination of platelet aggregation/adherence in blood during a hemostasis process(es).

Figure 6A:
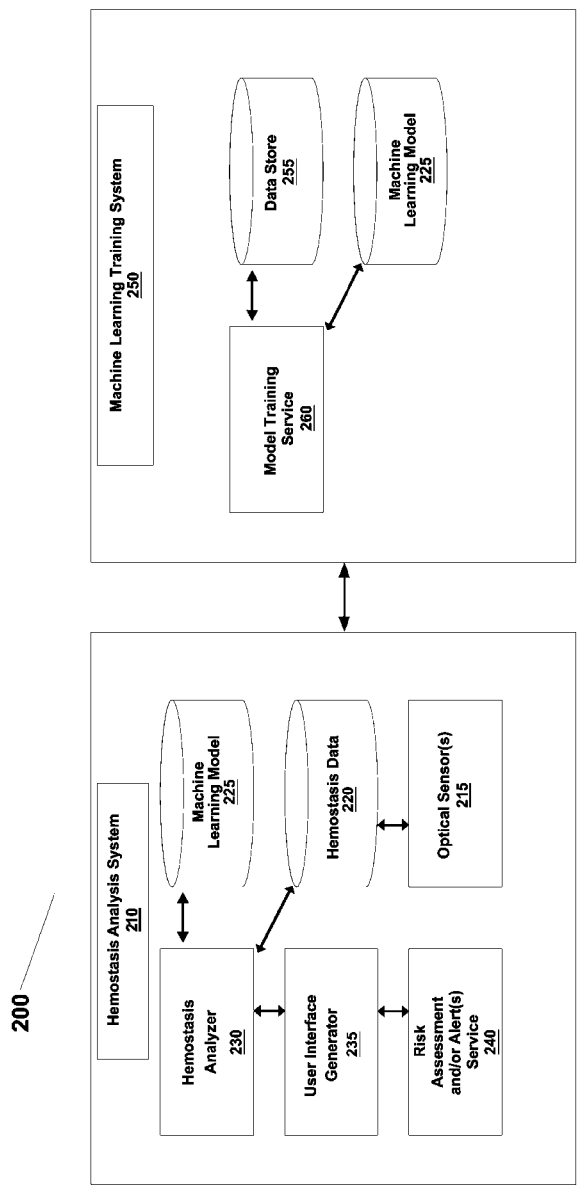
FIG. 6A illustrates an example system to provide an analysis of hemostasis as discussed herein, according to aspects of the disclosure.

FIG. 6A illustrates a hemostasis analysis system 200 that supports the analysis of images and/or other sensory information as described herein. The hemostasis analysis system 200 may include a measurement system to quantify the extent of hemostasis analysis system 210 and a machine learning training system 250. Although shown as separate components, in some embodiments, the hemostasis analysis system 210 and the machine learning training system 250 may be part of the same computer system. In some embodiments, the hemostasis analysis system 210 and the machine learning training system 250 may be remote components connected over a network. For example, the hemostasis analysis system 210 may be located on a personal device such as a mobile device, personal computer, smart watch or other device. The machine learning training system 250 may be located on the same device as the hemostasis analysis system 210 or on a remote device such as a central server.

In some embodiments, there may be fewer or additional components than shown in FIG. 6A. For example, while an optical sensor 215 is shown as part of hemostasis analysis system 200, in some embodiments, there may be different hemostasis detection sensors and/or devices (not described above) that are used in different parts of training a machine learning model and/or application stages of a machine learning model.

The machine learning training system 250 may include a model training service 260 and a hemostasis data store 255. Based on the model training service 260 and hemostasis data store 255, the machine learning training system 250 may produce a machine learning model 225 for use in the hemostasis analysis system 210. The hemostasis data store 255 may include hemostasis data associated with an individual that was recorded over a period of time. In some embodiments, the hemostasis data store 255 may include additional data associated with additional individuals. In another example, the hemostasis data store 255 may include images associated with known outcomes or results for use in training the machine learning model 225. For example, the machine learning training system 250 may train additional machine learning models associated with additional individuals based on data included in the hemostasis data store 255.

In some embodiments, the hemostasis data store 255 may further include labeled data indicating hemostasis levels for platelet aggregation/adherence phenomena at different times during which the hemostasis data was recorded. Accordingly, the hemostasis data store 255 may include data to train a machine learning model 225 via the model training service 260. The hemostasis data store 255 may include hemostasis data taken over a period of time including milliseconds, seconds, minutes, hours, days, months, years or longer. In some embodiments, the hemostasis data store 255 may include data associated with a set procedure or activity. For example, the hemostasis data store 255 may include data that is associated with surgery, health monitoring, patient medical history, existing or underlying conditions, predictive indicators, exercise, eating, or the like. Accordingly, platelet aggregation/adherence may be expected to remain stable during some procedures/activities and to change at a predictable rate during other activities and a model for the change during these procedures/activities can provide accurate labels for different samples of the hemostasis data.

In some embodiments, the hemostasis data store 255 may include hemostasis data for an individual associated with the hemostasis analysis system 200. For example, the hemostasis data store 255 may receive data from the hemostasis analysis system 200 that may be generated by optical sensors 215 and/or different sensors (not shown). Thus, as new data is added to the hemostasis data store 255, the model training service 260 may update or produce new machine learning models 225.

The machine learning model 225 may start as a generic machine learning model. For example, a machine learning model 225 trained with data associated with a general population may be used as a starting model for training a machine learning model 225 for an individual. In some embodiments, the machine learning model 225 may start with randomized values for a number of matrices within the model. The machine learning model 225 may be set with a number of convolutional layers, recurrent layers, or the like prior to training by the model training service 260, as will be understood by those skilled in the art.

Various machine learning models may be used. In some embodiments, a convolutional neural net, a recurrent neural net, various other types of neural nets, or some combination thereof may be used, as will be understood by those skilled in the art. For example, the machine learning model 225 may include multiple (e.g. 2, 3, 4 or more) convolutional layers and 1-2 (or more) fully connected layers. In some embodiments, fewer or additional layers of different types of layers may also be used. Furthermore, in some embodiments, drop out matrices, skip connection, max pooling, or other techniques may be used. In an example, the type of machine learning model utilized may be based on the amount and/or type of data available in the hemostasis data sore 255.

The training of the machine learning model 225 can be accomplished with a number of techniques, as further discussed below. Generally, the platelet aggregation/adherence assays will be input each with a known degree of platelet aggregation/adherence. Depending on the type of machine learning model, the platelet aggregation/adherence data may then be processed by a set of mathematical operations (e.g. addition, multiplication, convolution) involving weight matrices at more than one level in the machine learning model 225. After processing, the machine learning model 225 may then generate an output. Based on the output compared to the known level of platelet aggregation/adherence in each blood sample, the machine learning model 225 may be updated. For example, weight matrices may be updated using back propagation to better approximate the quantitative data during a next processing stage.

The process of training the machine learning model 225 may be repeated with various segments of the hemostasis analyzer data at different times using the labeled platelet aggregation/adherence data. The process may be repeated multiple times until the outputs of the machine learning model 225 are within a desired accuracy range. For example, the thresholds may be set to be within the confidence limits of the measured values at each point in time. The thresholds may also be set such that they are within a threshold of a measured value at least throughout a specified amount of time.

In some embodiments, training of the machine learning model 225 may be performed at a computer, computing system, or server capable of large amounts of data processing. For example, a computing or server system may be used for multiple individuals to train multiple machine learning models for each individual. However, in some embodiments, training of the machine learning model 225 may be performed on an individual's personal computer, mobile device, smart watch or other device. In some embodiments after training, the machine learning model 225 may be applied or transferred to a different computer system than that used for training. For example, a computing system or server system may be used to train the machine learning model 225 for an individual, however, after training, the machine learning model 225 may be applied on or transferred to the individual's personal computer, mobile device, smart watch, or the like. In some implementations, different servers, computer systems, personal computers, mobile devices, or the like may be used to perform any tasks as described herein.

The machine learning model 225 also may learn features and/or relations between features during training. Features may be extracted regarding the motion, geometry and/or physical appearance as platelet aggregation/adherence develops. Features characterizing free floating platelet aggregates and or adherent platelet aggregates in some embodiments include object radius, color, saturation, hue, curvature, location and/or general shape. Furthermore, certain subjects may have different features than those described above. Such individual differences may also be used to increase the sensitivity of the process or machine learning model 225.

In some embodiments, the machine learning model 225 may include or comprise a recurrent neural network. A recurrent neural network may receive sequential data as an input, such as consecutive images or synthetic representations, and then the recurrent neural network may update its internal state at every time step. The recurrent neural network may allow for accurate results in associated with temporal dynamic behavior (e.g., data of varying lengths of time). In some embodiments the machine learning model 225 may be a convolutional neural network. A convolutional neural network may include a number of convolutional layers that apply convolution operations using weight matrices and non-linearities to identify one or more features in the input data. The output of each convolutional layer may then be passed up to another layer to provide further analysis. In some additional embodiments, the machine learning model 225 may have a combination of recurrent and convolutional layers that identify and quantify different features in input data. In another example, other types of neural networks may be utilized, whether alone or as a combination.

A starting machine learning model may be created from a given patient, but the majority of training examples may be based on alterations directly from the artificial image or from vessel geometry from the starting model. Alternatively, the starting model or models are averages or other models not directly related to a given patient. Such data is synthetic by not being extracted from data for particular patients. The digital representation is generated and stored on a computer. In alternative embodiments, some or a majority of the training examples are extracted from patient-specific data for a plurality of patients and only some of the examples are alterations of those models. This added synthetic data may be used to get a richer representation, which may partially compensate for uncertainties in the data. To populate the database used in training the machine learning model 225, different approaches may be used. One or more baseline models, whose properties are then randomly or systematically perturbed to obtain a large number of models, are created. The baseline models may be represented by healthy population average hemostasis geometries, atlas models, and/or animal data. Other baseline models may be used. In another approach, each model is generated separately by following a set of rules and by randomly or systematically perturbing the parameter values of these rules. Scaling laws may be used for generating realistic synthetic models.

The model training service 260 may train a machine learning model 225 for an individual having data in the hemostasis data store 255. In some embodiments, the model training service 260 uses automatic statistical analysis of labeled data in order to determine which features to extract and/or analyze from an optical sensor and/or other sensors. The model training service 260 may determine which features to extract and/or analyze from a platelet aggregation/adherence assay based on labeled hemostasis data that the hemostasis data store 255 receives.

The hemostasis analysis system 210 in FIG. 6A may provide data from video images, or from a hemostasis sensor (e.g., an optical sensor 215) to store as hemostasis data 220. The hemostasis data 220 may then be applied to the machine learning model 225 by a hemostasis analyzer 230. The machine learning model 225 may be the same as was trained by machine learning training system 250 describe above. In some embodiments, the machine learning model 225, the hemostasis analyzer 230, or other components of the hemostasis analysis system 210 may be on a separate computing system or device than the hemostasis analysis system 210. For example, the machine learning training system 250 may include one or more components of the hemostasis analysis system 210.

The hemostasis analyzer 230 may apply the machine learning model 225 by providing inputs from the hemostasis data 220. As discussed herein, the hemostasis data may be pre-processed into set interval segments, averages, smoothed, noise reduced, or otherwise provided in a set manner to the hemostasis analyzer. The hemostasis analyzer 230 may apply the machine learning model 225 to hemostasis data 220 to generate an output of the measurement of soluble fibrin or platelet aggregation/adherence concentration and/or related processes.

In some embodiments, a user interface generator 235 may provide the analyzed data to a user interface. For example, the user interface generator 235 may generate a user interface including one or more outputs such as short-chain fibrin assay output, fibrin lattice formation assay output, platelet aggregation/adherence output, a further blood analysis output, or any component or combination thereof. For example, in some embodiments, a user interface generator 235 may provide a user interface as described with reference to FIG. 5D.

While shown as including a machine learning model 225 for particular hemostasis analyses, in some embodiments, the hemostasis analysis system 210 may provide additional data for soluble fibrin or platelet aggregation/adherence related data incorporating biological or synthetic components (such as a reagent or other chemical), morphology and processes. For example, machine learning training system 250 may provide multiple machine learning models 225 for different proteins or processes based on an individual's hemostasis data.

The user interface 300 illustrated in FIG. 5D shows an example output of a hemostasis analysis system which, when in use, may be on a separate computing system than the hemostasis data for an individual. FIG. 6C shows an example methodology for use of the platelet aggregation/adherence and/or other hemostasis readings from blood tests, which may be done on the same patient over time continuously or at intervals. The platelet aggregation/adherence assay results may then be combined with other measurements of the hemostasis analysis system 210 and the results singly or collectively may then be used with or without the employment of a machine learning model to determine whether an individual so studied is under threat from a clotting episode or a bleeding episode. This information is of considerable value in certain disease states where tissue damage is occurring or during certain surgical procedures such as solid organ transplants.

Figure 6B:
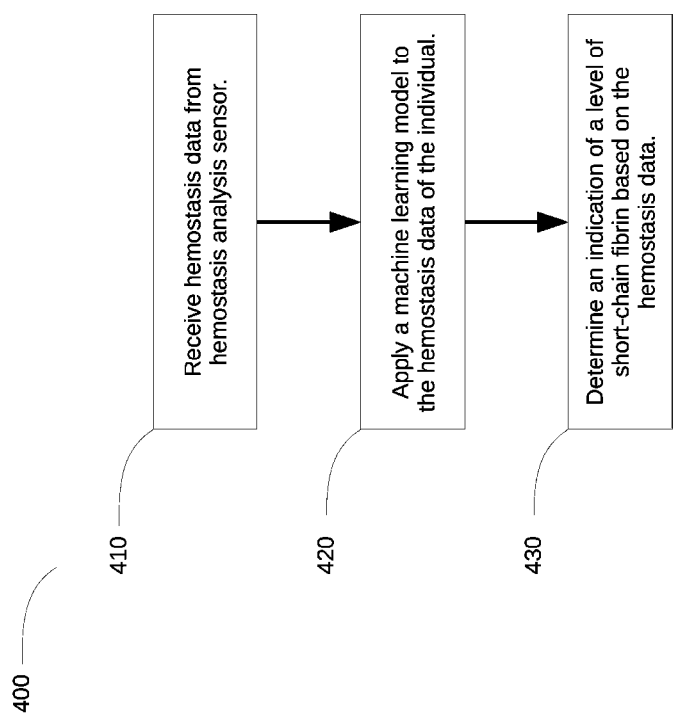
FIG. 6B illustrates a flow diagram of processes as performed by a hemostasis analysis system, according to aspects of the disclosure.
Figure 6C:
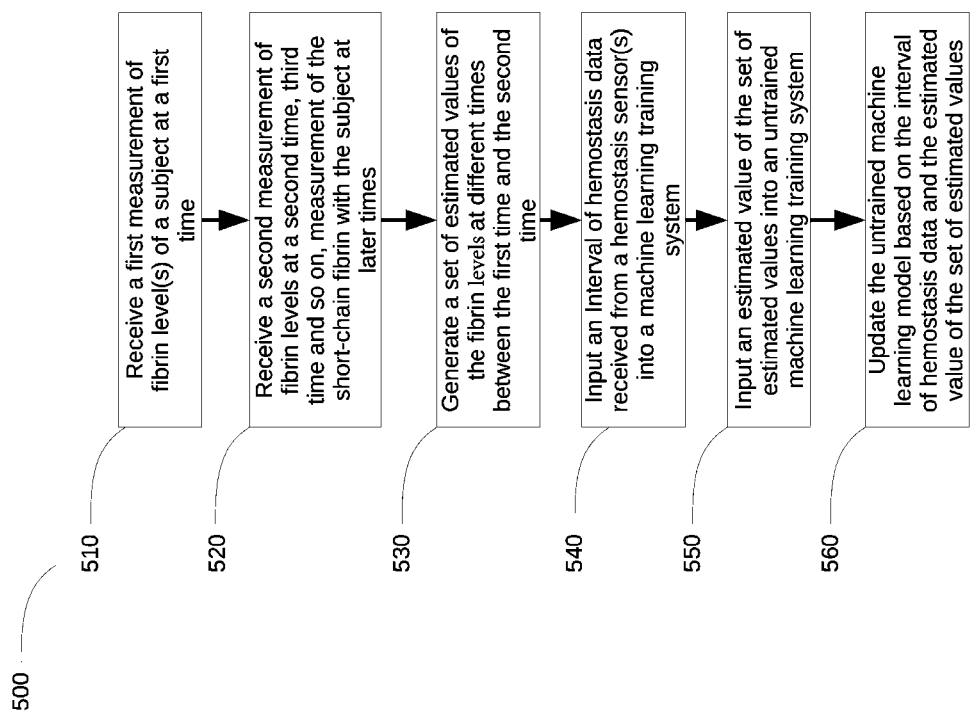
FIG. 6C illustrates a flow diagram of processes performed by a hemostasis analysis system, according to aspects of the disclosure.
Figure 6D:
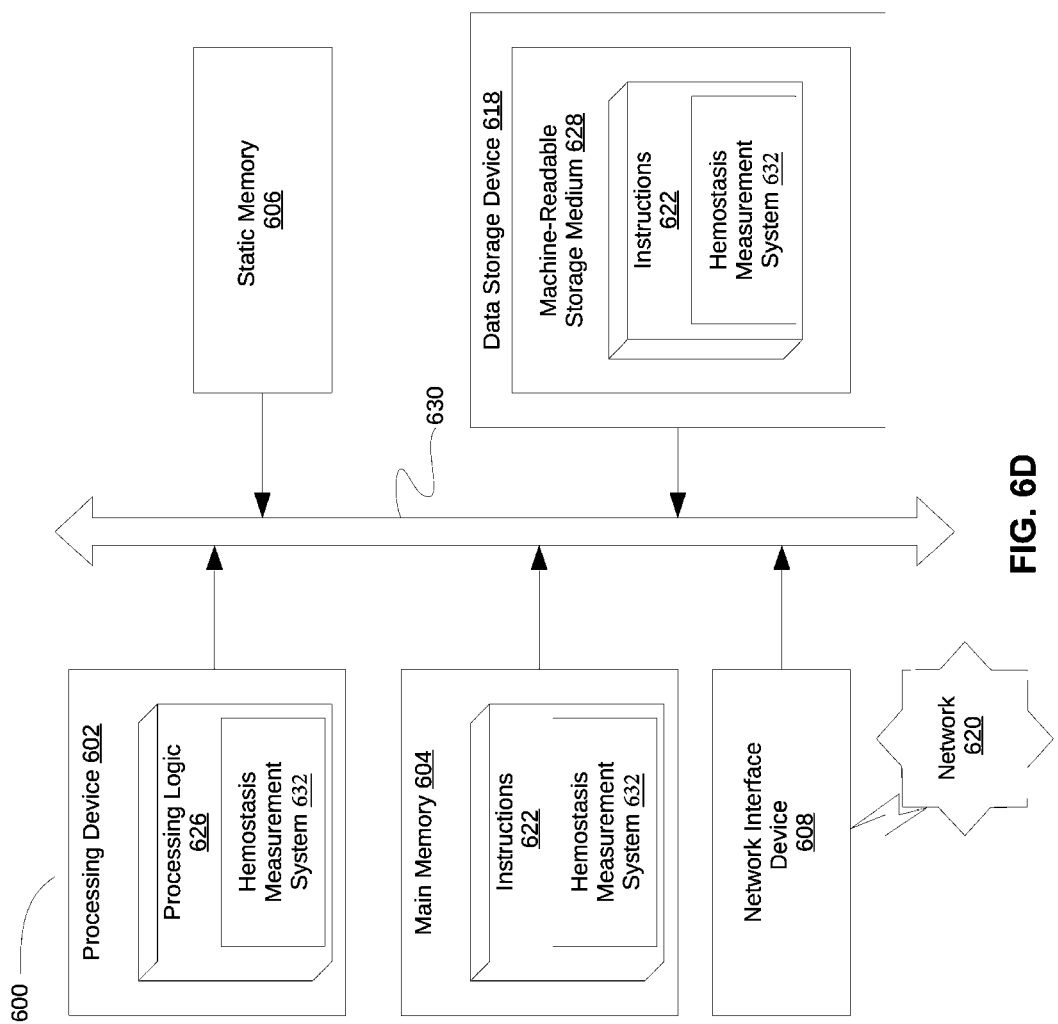
FIG. 6D illustrates an example computing environment of a hemostasis analysis system, according to aspects of the disclosure.
Figure 6E:
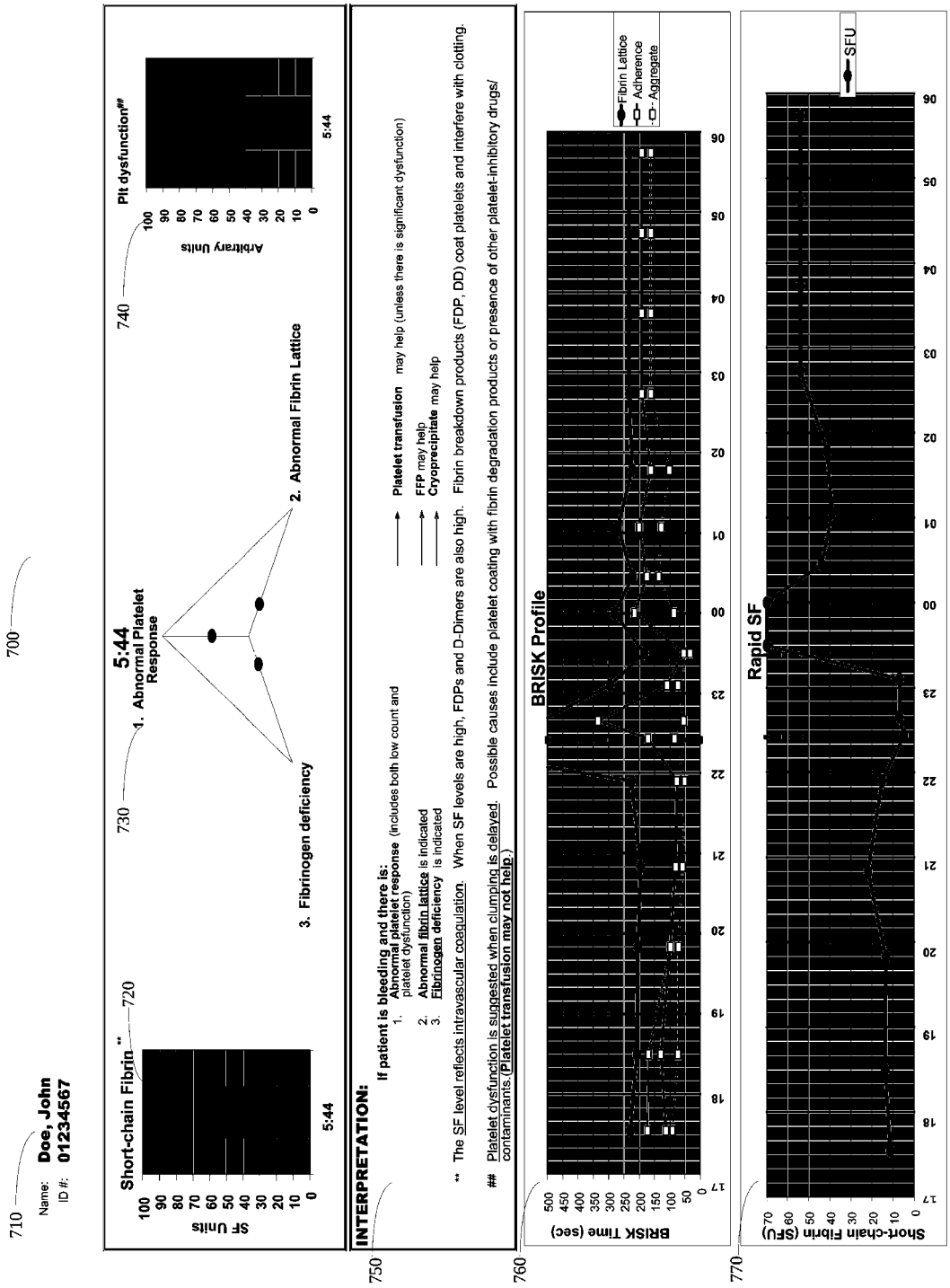
FIG. 6E illustrates an example output from the system for hemostasis analysis, according to aspects of the disclosure.

For example, the output 700 of data from the hemostasis analysis system 210 may include one of more of the several components shown in FIG. 6E, which are used to generate training data for the machine learning model. Data from a first hemostasis assay can be used to generate training data for the machine learning model. A second hemostasis assay and the third hemostasis assays are subsequent evaluations that may be used in hemostasis analysis systems 210. This may be used to generate algorithms that correlate measurements of various components of the hemostasis system for medical use. For example, FIG. 6E shows an output of data on platelet aggregation/adherence and data on lattice-fibrin assays are shown together with data on short-chain fibrin levels. As shown in FIG. 6C, the hemostasis data 220 analyzed by the machine learning model 225 during single or multiple hemostasis assay sessions may be correlated with other hemostasis data for additional findings and/or evaluations with or without the use of the machine learning model 225 and the embodiments of this data may exist and may or may not be displayed in part or composite. Hemostasis assays may be used singly or repetitively with or without additional hemostasis information and with or without the machine learning model 225. The machine learning model 225 can further be used to evaluate an individual's hemostatic competency at points between hemostasis assays. Accordingly, the hemostasis level(s) may be monitored for periods of high levels to recognize risk(s) to the individual between assays.

Hemostasis data from the machine learning training system 250, the hemostasis analysis system 210, or similar information may be correlated to patient condition(s). Such correlations, for example, may be utilized to determine existing hemostasis conditions, previous conditions or predictable conditions. Additionally, an alert service may use the data provided by the machine learning model 225, data flow 400, and/or data flow 500 to determine whether to alert the operator to potential additional issues with the levels of additional components of the hemostasis system; whether there is only a single reading; and/or whether a component is out of the normal range or multiple readings and/or components are out of range. Furthermore, with the addition of clinical information about the bleeding/clotting status of an individual the machine learning model 225 allows identification of patterns of abnormality in the interactions between the several assays or indicators. For example, as shown in user interface elements in charts 340 and/or 700 in some embodiments, a user interface may provide an alert and/or a recommendation. In some embodiments, an alert service may request or prompt a retest of certain of the hemostasis assay(s) prior to providing an alert to contact a physician, for example to correct a discrepancy located as described in FIG. 6C.

FIG. 6B depicts a data flow 400 illustrating the application of a machine learning model to a soluble fibrin assay profile of a subject. In some embodiments, the processes described with respect to FIG. 4 may be performed by one or more components of the hemostasis analysis system 200 as described with reference to FIG. 6A. Specifically, data flow 400 may be included in one or more programs, protocols, or instructions loaded into memory of the hemostasis analysis system 210 and/or the machine learning training system 250 and executed on the processor or one or more processors of the hemostasis analysis system 210 and/or the machine learning training system 250. The order in which the operations are described is not intended to be construed as a limitation, and any number of the described blocks may be combined in any order and/or in parallel to implement the data flow 400.

A hemostasis analysis system can be used for platelet aggregation/adherence assays, soluble fibrin assays or a clotting assay. In an embodiment as shown in FIG. 6B, beginning in block 410, a hemostasis analysis system 200 may receive a first measurement of a patient blood sample, with or without additional chemicals and/or reagents. In one embodiment, the first measurement of the patient blood sample may be received using an optical sensor 215 and/or images of blood sample(s) and/or reagent(s) with interaction recorded. For example, an individual may have a blood test run to determine hemostasis level(s) of the individual's blood prior to, concurrent to, and/or after performing a medical process or procedure. Beginning in block 410, a hemostasis analysis system may receive data from the hemostasis sensor. For example, the hemostasis sensor(s) may provide real-time data of an individual's blood sample and/or its interaction with specified reagents or other chemicals. In some embodiments, the hemostasis sensor(s) may be an optical sensor 215. In some embodiments, hemostasis analysis system sensor(s) may transmit an entirety, and/or subset(s), of data to process. Thereafter, as shown at 420, the hemostasis analysis system 200 may apply a machine learning model 225 to the status of hemostasis in the individual. In some embodiments, the machine learning model 225 has been trained based on previous hemostasis data associated with the subject and a source of a hemostasis measurement associated with the subject as described above. For example, the machine learning model 225 may be specific to an individual based on prior measurements.

In block 430, the hemostasis analysis system 200 may determine an indication of a level(s) of soluble fibrin or platelet aggregation/adherence based on the hemostasis data. For example, the hemostasis analysis system 200 may determine whether the individual's soluble fibrin or platelet aggregation/adherence level(s) for a target hemostasis level(s) are higher or lower than expected or healthy. The hemostasis analysis system 200 may also determine hemostasis to be in a normal range. Furthermore, the hemostasis analysis system 200 may determine a specific estimated level(s) of the individual's platelet aggregation/adherence levels, in some embodiments.

FIG. 6C depicts a data flow 500 illustrating the application of a machine learning model to the hemostasis data of a subject obtained from the soluble fibrin assay. In some embodiments, the processes described with respect to FIG. 6C may be performed by one or more components of the hemostasis analysis system 200 as described with reference to FIG. 6A. Specifically, data flow 400 may be included in one or more programs, protocols, or instructions loaded into memory of the hemostasis analysis system 210 and/or the machine learning training system 250 and executed on the processor or one or more processors of the hemostasis analysis system 210 and/or the machine learning training system 250. The order in which the operations are described is not intended to be construed as a limitation, and any number of the described blocks may be combined in any order and/or in parallel to implement the data flow 400.

Beginning in block 510, a hemostasis analysis system may receive a first measurement of hemostasis phenomenon/phenomena, such as soluble fibrin levels or the platelet aggregation/adherence levels, within a subject and/or sample at a first time. For example, a sample and/or individual may have a blood test run to determine a level of hemostasis prior to performing a process or procedure. In block 520, the hemostasis analysis system 200 may receive a second measurement, third measurement, and so on of hemostasis phenomenon/phenomena within a subject and/or sample at a second time, third time, and so on, respectively. For example, a subject or individual may have a blood test run to determine level of hemostasis before and/or after performing a process or procedure and/or during a process or procedure. Although described as two measurements, in various embodiments, fewer or additional measurements may be used to determine hemostasis level(s). In block 530, the hemostasis analysis system 200 generates a set of values representing the hemostasis of an individual and/or sample at the second instance. In some embodiments, as discussed herein, additional measurements from a different machine may be used by the hemostasis analysis system 200. Furthermore, in some embodiments, a single measurement could be taken, and an action performed that cause hemostasis level(s) to vary in a predictable manner.

For example, a measurement could be taken at the beginning of a medical or surgical treatment session and additional values may be generated from the measurement based on the individual's known condition(s) and/or medical history, age, biological sex, and/or other factors. In another embodiment, a specific drug may be administered that is known to accumulate in the bloodstream in a predictable manner over time. Similarly, ingestion of food may be used where the absorption of sugar, fats, proteins, vitamins, minerals, or the release of insulin or other enzymes or metabolites or chemical(s) may affect the platelet aggregation/adherence level(s) and/or phenomena.

At 540, the hemostasis measurement may be received from a sample into a machine learning training system 250. In block 550, the hemostasis analysis system 200 may use hemostasis level(s) generated from the measured value (or values) as a label input into the machine learning training system 250. Such an example may provide the machine learning training system 250 with data to determine the accuracy of the machine learning model 225. In block 560, the hemostasis analysis system may update the machine learning model 225 based on the sensor data of platelet aggregation/adherence and estimated presence or absence of soluble fibrin. In one embodiment, the hemostasis analysis system 200 may update weight matrices applied by a convolutional or recurrent machine learning models.

FIG. 6D illustrates a diagrammatic representation of an example a computer system 600 within which a set of instructions, for causing the system for hemostatic analysis of blood and/or other fluids to perform any one or more of the methodologies discussed herein, may be executed. In alternative embodiments, the computer system 600 may be connected (e.g., networked) to or in signal communication with other computer systems or devices in a local area network (LAN), an intranet, an extranet, or the Internet. The computer system 600 may operate in the capacity of a server or a client machine in a client-server network environment, or as a peer machine in a peer-to-peer (or distributed) network environment. The computer system 600 may be a personal computer (PC), a tablet PC, a set-top box (STB), a Personal Digital Assistant (PDA), a cellular telephone, a web appliance, a server, a network router, a switch or bridge, a hub, an access point, a network access control device, or any machine capable of executing a set of instructions (sequential or otherwise) that specify actions to be taken by that computer system 600. Further, while only a single computer system 600 is illustrated, the terms "computer system", "machine", and/or "device" shall also be taken to include any collection of computer systems that individually or jointly execute a set (or multiple sets) of instructions to perform any one or more of the methodologies discussed herein. In one embodiment, computer system 600 may be representative of a server, such as one or more components of a hemostasis analysis system (e.g., hemostasis measurement and analysis system 632) configured to perform processes as described above.

The exemplary computer system 600 includes a processing device 602, a main memory 604 (e.g., read-only memory (ROM), flash memory, dynamic random access memory (DRAM), a static memory 606 (e.g., flash memory, static random access memory (SRAM), etc.), and a data storage device 618, which communicate with each other via a bus 630. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Processing device 602 represents one or more general-purpose processing devices such as a microprocessor, central processing unit, or the like. More particularly, the processing device may be a complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, a central processing unit (CPU), a semiconductor-based microprocessor, a graphics processing unit (GPU), a real time processor (RTP), or the like. The processing device 602 is configured to execute processing logic 626 or instructions, such as shown in FIGS. 6B-6C, for performing the operations and steps discussed herein.

The data storage device 618 may include a machine-readable storage medium 628, on which is stored one or more set of instructions 622 (e.g., software) embodying any one or more of the methodologies of functions described herein, including instructions to cause the processing device 602 to execute operations of the hemostasis measurement and analysis system 632. The instructions 622 may also reside, completely or at least partially, within the main memory 604 or within the processing device 602 during execution thereof by the computer system 600; the main memory 604 and the processing device 602 also constituting machine-readable storage media. The instructions 622 may further be transmitted or received over a network 620 via the network interface device 608. For example, during an initiation, startup, or at any other point, the instructions 622 may be loaded into the main memory 604 over the bus 630. The processing device 602 may then execute the instructions 622. The instructions 622 may be represented by each of the blocks in data flow 400 and/or data flow 500. Other instructions may be included in the hemostasis measurement and analysis system 632 to perform various other operations as described herein.

The machine-readable storage medium 628 may also be used to store instructions to perform a method for hemostasis measurement and analysis systems, as described herein. While the machine-readable storage medium 628 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

Additionally, some embodiments may be practiced in distributed computing environments where the machine readable medium is stored on and or executed by more than one computer system. In addition, the information transferred between computer systems may either be pulled or pushed across the communication medium connecting the computer systems.

The output 700 of data from the hemostasis analysis system 210 may include one of more of the several components shown in FIG. 6E. For example, the output 700 can include personal identifying information 710 of the individual. The output 700 can include data about the soluble fibrin measurements 720 or the platelet function measurements 740 from the blood of the individual. These measurements of one or more hemostatic status of an individual can be provided in the form of a star diagram 730 to provide decision support to a healthcare professional. In a star diagram 730, the fibrinogen deficiency, the clotting time, and the platelet function of a patient sample are plotted on the x, y, and z axis. The further a particular data point is from the origin, the more abnormal is that particular endpoint as compared to a reference sample from a healthy individual. These measurements of one or more hemostatic status of an individual as provided in the form of a star diagram 730 may be accompanied by an interpretation panel 750 that also provides recommended treatment modalities. For example, based on the star diagram 730, if there is an abnormal platelet response and an observation of bleeding in the individual, then a recommendation for a platelet transfusion is provided. Based on the star diagram 730, if there is an abnormal fibrin lattice response and an observation of bleeding in the individual, then a recommendation for administration of fresh frozen plasma (FFP) is provided. Based on the star diagram 730, if there is an indication of fibrinogen deficiency and an observation of bleeding in the individual, then a recommendation for administration of a cryoprecipitate is provided. Such a cryoprecipitate contains a concentrated subset of FFP components including one or more of fibrinogen, Factor VIII coagulant, von Willebrand factor, and Factor XIII.

As illustrated in FIG. 6E, the output 700 of data from the hemostasis analysis system 210 may include a bleeding risk profile (BRISK Profile). A BRISK profile is a graphical plot that includes an overlay of time-based monitoring of one or more endpoints, such as platelet aggregation, platelet adhesion to the inner wall of a sample container, and clotting. In certain embodiments, this BRISK profile 760 is provided in an operating room during surgery (for example during organ transplantation (most often during liver transplantation)) to determine whether disseminated intravascular coagulation (DIC) is present and, if the patient is bleeding, what transfusion modalities are likely to be most helpful. As illustrated in FIG. 6E, the output 700 of data from the hemostasis analysis system 210 may include a graphical plot 770 that includes an overlay of time-based monitoring of soluble fibrin levels.

Figure 6F:
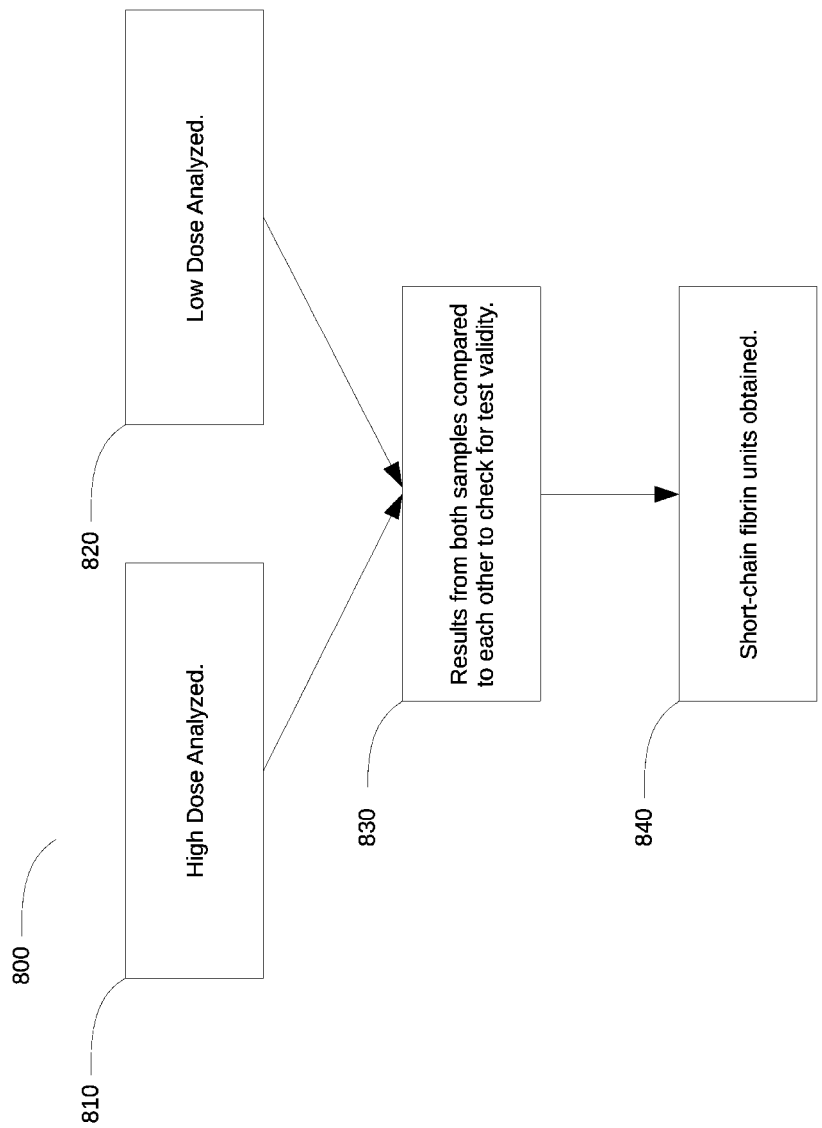
FIG. 6F illustrates an example operation to verify and validate the hemostasis analysis system, according to aspects of the disclosure.

The hemostasis analysis system 200 and/or assays generated may be verified in whole or in part, including but not limited to the reagents used in combination with the subject's sample. For example, FIG. 6F represents a sample with reagents (cuvette #1) 810 and a second sample with reagents (cuvette #2) 820 on the same individual being performed simultaneously so the results may be used to verify adequacy of the soluble fibrin assay and assure that the reagents utilized and the procedures being followed are functioning correctly. At block 830, the results from both samples may be compared to determine or check for validity. At block 840, the soluble fibrin measurement may be obtained from the samples. This soluble fibrin measurement may further be stored in the hemostasis data store 255.

An interplay between platelet aggregation and the coagulation cascade defines normal hemostasis. If hemostatic competence of an individual is to be assessed, the in vitro assessment must be rapid as several of the chemical species that affect the process have half-lives measured in seconds and will decay rapidly after withdrawal of a blood sample from the circulation. The assessment of platelet function and coagulation should occur concurrently as these processes are physiologically interactive at several points during hemostasis, each driving the other. In an embodiment, the methods of assessing hemostatic competence of an individual includes performing repetitive assessments of time-to-appearance of one or more of the several endpoints of hemostasis described in this disclosure. In certain instances, the image analysis system is used to generate an x-y curve that documents one or more of the several endpoints of hemostasis and then to determine area under that curve during a specified time period of observation. This area under the curve is compared against a previously determined reference range and the z score attributable to the blood sample under analysis is calculated to assess the hemostatic competence of the individual. These quantified measurements of area under curve are also used to differentiate between normal and abnormal events of diagnostic significance at the point-of-care of a patient or in the clinical laboratory. Performing assessments of hemostatic competence immediately after removing blood from the human vascular system provides accurate measurements of in vivo levels of responsiveness of blood cellular elements. Provided here are methods of determining various endpoints of hemostasis including platelet aggregation and coagulation. In an embodiment, these methods are performed within seconds of removal of the sample from circulation. Also disclosed here are various reagents and kits to facilitate the methods of determining various endpoints of hemostasis including platelet aggregation and platelet-induced coagulation in response to platelet agonists. The various endpoints that are monitored are: (i) aggregates of platelets that are larger in diameter than 0.5 mm; (ii) adhesion of platelets to the inner wall of the rotating sample container, (iii) appearance of polymerized fibrin, (iv) movement of a clot spiral, (v) secondary attachment of the platelet aggregates to the inner wall, (vi) formation of soluble fibrin precipitates, and (vii) formation of fibrin nets that entrap and bind the blood cellular element forming a blood clot.

Figure 7:
FIG. 7 is an image of a sample container with a blood sample that contains platelet aggregates (about 0.5 mm in diameter). This is an early endpoint of hemostasis evaluated by a system for platelet function and coagulation analysis according to one embodiment of the present disclosure.

Disclosed here is a method for evaluating platelet aggregation properties of a blood sample from a patient. One such method includes the steps of depositing a portion of the un-anticoagulated whole blood sample from a patient or other blood donor into a sample container, placing the sample container into the sample container assembly, incubating the portion of the un-anticoagulated whole blood sample in the sample container under specified temperature and reaction conditions, and monitoring formation of aggregates of platelets that are larger than 0.5 mm. FIG. 7 is an image of a sample container with a blood sample that contains platelet aggregates (about 0.5 mm in diameter). In an embodiment, the time elapsed from the initiation of the reaction to the observation of 4 to 5 aggregates of platelets in the blood sample, each 0.5 mm in diameter or larger, is recorded and compared against such time for similar platelet aggregation in control blood samples. The time for formation of platelet aggregates can be measured by image analysis system or by photo-optical measurement of light transmission. In an embodiment, the time for formation of platelet aggregates is measured by detection of platelet aggregates using light transmission aggregometry. The detection and recording of formation of platelet aggregates can be detected in white light. In certain embodiments, increasing wavelength of the light to the range of wavelengths corresponding to red light will enhance the ease of detecting and make the detection process more reproducible. In another embodiment, the formation of platelet aggregates is monitored by image analysis to determine the characteristics of the endpoint, such as size or growth of the platelet aggregates over a pre-defined time period. The images of the platelet aggregates are processed and subjected to background subtraction, and this data is used to calculate the time to arrive at an endpoint, such as size (larger than 0.5 mm) or growth of the platelet aggregates over a pre-defined time period. The time to the formation of the first aggregates and the subsequent rate of growth of platelet aggregates can be used to estimate the number of platelets or the size of the platelet mass or both in a blood sample. This information assists medical professionals to order and administer various blood component to a bleeding patient. Using data from the image analysis and other reaction data, such as time taken to reach the endpoint, one can diagnose a physical condition or continue/modify a treatment protocol for a patient. For example, lengthening of the time for formation of platelet aggregates is indicative of insufficient platelets or abnormal platelet function and, consequently, an increased risk of excessive bleeding or hemorrhage. Shortening of the time for formation of platelet aggregates is indicative of hyperactive platelet functioning or of an increased number or increased mass of platelets and, consequently, of a tendency to thrombosis. Changes in the time for formation of platelet aggregates can be used to screen for different diseases, such as bone marrow disorders, uremia, autoimmune disorders, von Willebrand disease, etc. Changes in the time for formation of platelet aggregates can also be used to monitor efficacy of medications that affect platelet aggregation, such as antibiotics, antihistamines, antidepressants, platelet acetylating agents (such as aspirin), nonsteroidal inflammatory drugs (NSAIDS), and platelet inhibiting agents (such as clopidogrel, prasugrel, etc.). Changes in the time for formation of platelet aggregates can also be used to monitor platelet function in surgical settings for evaluating bleeding risks and efficacy of different prohemostatic therapies. The surgical settings can include catheterization, cardiac surgery, surgery, organ transplant, or dialysis. In an embodiment, the times to aggregate formation are in the order of 100-150 seconds immediately upon blood withdrawal and shorten to 50-65 seconds by 45 minutes post-specimen acquisition. However, these times vary widely in disease states. In an embodiment, the samples are analyzed immediately upon collection. The sample containers may be immediately swirled to wet the walls before being placed the sample container assembly. In an embodiment, the whole blood sample is maintained at 37° C. prior to testing. Reaction conditions can include adding a portion of the whole blood sample to a pre-warmed sample container. The sample containers are maintained at a specified temperature ranging from 25 to 40° C. Reaction conditions can include the presence of one or more disclosure reagents and/or activators in the sample container, such as diatomaceous earth, or kaolin, or combinations thereof. The diatomaceous earth can be calcined diatomaceous earth. The diatomaceous earth can be Celite® diatomaceous earth (available from Sigma-Aldrich located in St. Louis, Missouri, USA). Reaction conditions can include the presence of one or more of components in the sample container, such as glass beads. Reaction conditions include the sample containers being subjected to one or more of a longitudinal rocking motion, lateral motion, and rotational motion in one or more directions.

Figure 8:
FIG. 8 is an image of sample containers with blood samples where the platelet aggregates have adhered to the inner walls of the sample container. This is another endpoint of hemostasis evaluated by a system for platelet function and coagulation analysis according to one embodiment of the present disclosure.

The platelet aggregates coalesce into larger masses that rapidly increase in size and adhere to the walls of the sample container. Disclosed here is a method for evaluating platelet adhesion properties of a blood sample from a patient. One such method includes the steps of depositing a portion of the whole blood sample from a patient into a sample container, placing the sample container into the sample container assembly, and monitoring adhesion of platelets to the inner walls of the sample container by the image analysis system. FIG. 8 is an image of sample containers with blood samples where the platelet aggregates have adhered to the inner walls of the sample container. The images are captured continuously or periodically at certain intervals, by the camera and sent to the analyzer controller that processes the images along with background subtraction. The images are further processed to obtain area occupancy on the inner wall of the sample container as an indicator of platelet adhesion. The percentages of area occupancy are plotted as a function of time. In an embodiment, the rate at which the clumps increase in size is measured as this measurement relates directly to the platelet count as it reflects the total mass of functional platelets. In an embodiment, the adhesion of platelets to the inner walls of the sample container is measured by light transmission analysis. Using data from the image analysis and other reaction data, such as time taken to reach the endpoint, one can diagnose a physical condition or continue/modify a treatment protocol for a patient. For a blood sample from a normal healthy individual, the platelet aggregates adhere to the walls of the sample container within typically 130-150 seconds immediately after sample acquisition shortening to 50-90 seconds as the short-lived platelet inhibitors that are produced by vascular endothelium disappear. For example, changes in the adhesion of platelets to the inner walls of the sample container are indicative of insufficient platelets or abnormal platelet function, and consequently an increased risk of excessive bleeding or hemorrhage. Changes in the adhesion profile of platelets to the inner walls of the sample container can be used to screen for different diseases, such as renal failure, thrombasthenia, thrombocytopenia, thrombocytosis, and von Willebrand disease. Changes in the adhesion profile of platelets to the inner walls of the sample container can also be used to monitor efficacy of medications that affect platelet adhesion, such as acetylsalicylic acid (ASA), clopidogrel, prasugrel, and the like. Changes in the adhesion profile of platelets to the inner walls of the sample container can also be used to monitor platelet function in surgical settings for evaluating platelet damage due to mechanical trauma in heart-lung machines and following protamine administration at the conclusion of open-heart surgery. The surgical settings can include heart vessel grafts, heart transplants, heart valve replacement/repair, liver transplants, orthopedic procedures, neurosurgical procedures, and trauma surgery. In an embodiment, the samples are analyzed immediately upon collection. Reaction conditions can include adding a portion of the whole blood sample maintained at 37° C. to a pre-warmed sample container. The sample containers are maintained at a specified temperature ranging from 25 to 40° C. Reaction conditions can include the presence of one or more of activators in the sample container, such as diatomaceous earth, or kaolin, or combinations thereof. The diatomaceous earth can be calcined diatomaceous earth. The diatomaceous earth can be Celite® diatomaceous earth. Reaction conditions can include the presence of one or more of additional components in the sample container, such as platelet agonists arachidonic acid, adenosine diphosphate, epinephrine, collagen, and ristocetin. Other additional components may also be added to aid in detection of endpoint, such as glass beads. Reaction conditions include the sample containers being subjected to one or more of a longitudinal rocking, motion, lateral motion, and rotational motion in one or more directions. As noted above the "normal" time for platelet adhesion depends upon how long the sample has been out of the human circulation and is no longer being inhibited by substances produced therein. Platelet clumping and the elapsed times to platelet clumps adhering to the wall of the sample containers shorten over the first 45 minutes eventually reaching an asymptomatic "plateau" at which point they remain relatively stable for one-two hours thereafter. Some tests are run in "plateau" such as exposing platelets to agonists. Other test such as measuring the area under curve are run during specified time periods such as the first 15 minutes after acquisition of the sample or the first 60 minutes.

In an embodiment, after the adhesion of platelets to the inner walls of the sample container is observed, a secondary endpoint is also detected whereby the platelet aggregates detach from the inner wall, resume free motion for a short period of time and then adhere again to the inner wall. Disclosed here is a method for evaluating secondary platelet adhesion properties of a blood sample from a patient. One such method includes the steps of depositing a portion of the un-anticoagulated whole blood sample from a patient into a sample container, placing the sample container into the sample container assembly, and monitoring adhesion of platelet aggregates followed by detachment and secondary adhesion of platelet aggregates to the inner walls of the sample container by the image analysis system. The images are captured continuously or periodically at certain intervals, by the camera and sent to the analyzer controller that processes the images along with background subtraction. The images are further processed to measure the time elapsed from initiation of reaction and adhesion of platelets to the inner walls of the sample container as an indicator of platelet function. Subsequently, the images are further processed to measure the time elapsed from initiation of reaction and secondary adhesion of platelet aggregates to the inner walls of the sample container as an indicator of platelet function.

Figure 10:
FIG. 10 is an image of sample containers with blood samples that contain soluble fibrin precipitates. This is another analytical endpoint evaluated by a system for platelet function and coagulation analysis according to one embodiment of the present disclosure.

Soluble fibrin is composed of fibrin monomers and short polymers which are well below the concentration necessary to produce a visible blood clot and are kept in solution by complexing with the relative excess of fibrinogen molecules in the blood. The fibrin molecule is negatively charged and is precipitated out of the blood sample by adding a positively charged molecule (e.g. protamine). Disclosed here is a method for evaluating the quantity of soluble fibrin in a blood sample from a patient. One such method includes the steps of treating a whole blood sample with a citrate solution, depositing a portion of the citrated whole blood sample from a patient into a sample container containing protamine, placing the sample container into the sample container assembly, and measuring time until formation of a soluble fibrin precipitate is detected by the image analysis system. The images are captured continuously, or periodically at certain intervals, by the camera and sent to the analyzer controller that processes the images along with background subtraction. The images are further processed to obtain the first instance of appearance of an endpoint defined as an appearance of a soluble fibrin precipitate of a diameter equal to or greater than 0.5 mm. This precipitate can be in one of two forms—either coarse reddish clumps which usually appear in the central portion of a sample container or transparent gel fragments that gather along the standing wave that forms along the down-sweeping fluid margin. FIG. 10 is an image of sample containers with blood samples that contain soluble fibrin precipitates. Time was measured until the first development of any precipitate with a diameter of at least 0.5 mm. Measurements were stopped at 300 seconds. Raw soluble fibrin times were then converted to arbitrary soluble fibrin units (SFU) measured as per second as follows:

$$SFU(s^{-1}) = \frac{700}{(SF \text{ time measured in seconds})}$$

Based on the SFU, one can diagnose a physical condition or continue/modify a treatment protocol for a patient. If the amount of soluble fibrin present in the patient's blood sample is significantly above the normal range, then a form of disseminated intravascular coagulation (DIC) is present. If this patient is bleeding, then determination of SFU can help with choosing an appropriate transfusion modality. In an embodiment, the normal range of SFU for healthy females is less than 11 and for healthy males is less than 9. For example, changes in the SFU are indicative of a differential risk of bleeding or clotting. Changes in the SFU can be used to screen for different diseases, such as incipient thrombosis or other embolism phenomena. Increase or decrease in the SFU can also be used to monitor clotting issues in hospital settings, such as monitoring development or resolution of disseminated intravascular coagulation during liver transplant surgery. Increase or decrease in the SFU can also be used to monitor and administer anticoagulation protocols of all types for hospitalized or ambulatory patients, including pregnant patients suffering from massive hemorrhage, DVTs, PEs, pre-eclampsia, envenomation, and massive trauma. In an embodiment, the samples are analyzed immediately upon collection or after a delay of several hours provided the sample is maintained at body temperature during the storage period. Reaction conditions can include adding a portion of the warm whole blood sample to a pre-warmed sample container. The sample containers are maintained at a specified temperature ranging from 25 to 40° C. Reaction conditions include the sample containers being subjected to one or more of a longitudinal rocking motion, lateral motion, and rotational motion in one or more directions. In an embodiment, the sample containers are gently subject to a rotational oscillation around the longitudinal axis at a rate of 15±1 rpm, while maintaining the reaction temperature at approximately 37° C.

As soluble fibrin levels continue to increase, however, they eventually reach a threshold concentration where fibrin-fibrin polymerization interactions prevail—and insoluble fibrin clot is formed. Disclosed here is a method for evaluating appearance of polymerized fibrin from a blood sample from a patient. One such method includes the steps of neutralizing a citrate anticoagulated whole blood sample with a calcium solution, depositing a portion of the treated whole blood sample from a patient into a sample container, placing the sample container into the sample container assembly, and measuring time until a polymerized fibrin endpoint is detected by the image analysis system. The images are captured continuously or periodically at certain intervals, by the camera and sent to the analyzer controller that processes the images along with background subtraction. The images are further processed to obtain the first instance of a rough irregular profile that develops at the leading edge of the miniature stationary wave that characterizes an edge of the fluid contained in the rotating sample container. The smooth edge of the fluid that constantly curls under the bulk of the fluid transforms to a rough irregular edge where the liquid of the treated blood sample encounters the interwoven fibrin strands adhered to the inner wall of the rotating sample container. This is the earliest appearance of the clotting endpoint and it usually coincides with the entrapment and removal of the glass beads if these are present. In an embodiment, the samples are analyzed immediately upon collection. Reaction conditions can include adding a portion of the whole blood sample to a pre-warmed sample container. The sample containers are maintained at a specified temperature ranging from 25 to 40° C. Reaction conditions include the sample containers being subjected to one or more of a longitudinal rocking motion, lateral motion, and rotational motion in one or more directions. In an embodiment, the sample containers are gently subjected to a rotational oscillation around the longitudinal axis at a rate of 15±1 rpm and rocked at 15 cycles per minute while maintaining the reaction temperature at approximately 37° C.

Figure 9A:
FIGS. 9A and 9B are images of sample containers with blood samples and glass beads at the initiation of hemostasis (FIG. 9A) and at an endpoint when the glass beads are entangled in fibrin strands (FIG. 9B). This is another endpoint of hemostasis evaluated by a system for platelet function and coagulation analysis according to one embodiment of the present disclosure.
Figure 9B:

Another method for evaluating appearance of polymerized fibrin from a blood sample from a patient includes the steps of treating an anticoagulated whole blood sample with a calcium solution, depositing a portion of the un-anticoagulated whole blood sample from a patient into a sample container with glass beads, placing the sample container into the sample container assembly, and measuring time until a polymerized fibrin endpoint is reached by the image analysis system. FIGS. 9A and 9B are images of sample containers with blood samples and glass beads at the initiation of hemostasis (FIG. 9A) and at an endpoint when the glass beads are entangled in fibrin strands (FIG. 9B). The images are captured continuously or periodically at certain intervals, by the camera and sent to the analyzer controller that processes the images along with background subtraction. The images are further processed to obtain the first instance of adhesion of the rotating glass beads to the inner wall of the rotating sample container. In an embodiment, the glass beads are 0.5 millimeter glass beads or other similar spherical particles that are added to the whole blood sample. As the sample container rotates, the glass beads also rotate around their own axes and remain more-or-less stationary at the low point of the rotating container. As the fibrin strands form, the strands entrap these glass beads and affix them to the inner wall of the rotating container. Appearance of the affixed glass beads is indicative of a polymerized fibrin endpoint in the hemostatic process. The normal time of clotting of the initial sample is 135-165 seconds and this range shortens by about 15 seconds as the sample sits in the 37° C. block. In an embodiment, the samples are analyzed immediately upon collection. Reaction conditions can include adding a portion of the whole blood sample to a pre-warmed sample container. The sample containers are maintained at a specified temperature ranging from 25 to 40° C. Reaction conditions include the sample containers being subjected to one or more of a longitudinal rocking motion, lateral motion, and rotational motion in one or more directions. In an embodiment, the sample containers are gently subject to a rotational oscillation around the longitudinal axis at a rate of 15±1 rpm and rocked linearly at 15 complete cycles per minute, while maintaining the reaction temperature at approximately 37° C.

Figure 11:
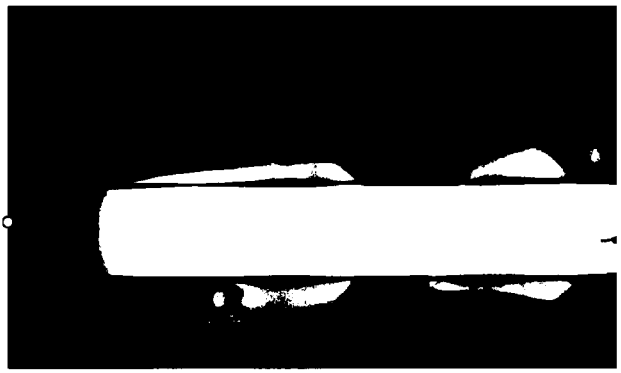
FIG. 11 is an image of sample containers with blood samples that contains a clot spiral attached at one end to an inner wall of the sample container. This is another endpoint of hemostasis evaluated by a system for platelet function and coagulation analysis according to one embodiment of the present disclosure.

If the fibrinogen concentration in the sample is below normal as the clot forms, it may attach to the inner wall of the sample container at only one rather than at many locations. Under these conditions, the clot may continue to grow and becomes a three-dimensional spiral of polymerized fibrin platelet aggregates and trapped red and white blood cells. FIG. 11 is an image of sample containers with blood samples that contains a clot spiral attached at one end to an inner wall of the sample container. Disclosed here is a method for evaluating clotting properties of a blood sample from a patient. One such method includes the steps of depositing a portion of the whole blood sample from a patient into a sample container with calcium ions to neutralize the contained citrate anticoagulant, placing the sample container into the sample container assembly, and monitoring formation of a clot inside the sample container by the image analysis system. The images are captured continuously or periodically at certain intervals, by the camera and sent to the analyzer controller that processes the images along with background subtraction. The images are further processed to measure the time elapsed from initiation of reaction and formation of a clot as an indicator of clotting function. Using data from the image analysis and other reaction data, such as time taken to reach the endpoint, one can diagnose a physical condition or continue/modify a treatment protocol for a patient. For example, changes in the time to form the clot are indicative of abnormal clotting function or an increased risk of excessive bleeding or hemorrhage. Changes in this particular clotting time since it is performed in whole blood with platelets playing their normal physiological role can be used to screen for the in vivo effectiveness of all clinically useful anticoagulants, such as heparin, Coumadin, hirudin, and the oral anti Xa agents. Changes in the clotting time can also be used to monitor patients in surgical settings for the determination of bleeding caused by coagulopathies versus inadequate mechanical hemostasis. In an embodiment, the samples are analyzed immediately upon collection. Reaction conditions can include adding a portion of the whole blood sample to a pre-warmed sample container. The sample containers are maintained at a specified temperature ranging from 25 to 40° C. Reaction conditions can include the presence of one or more of disclosure reagents in the sample container, such as diatomaceous earth, or kaolin, or combinations thereof. The diatomaceous earth can be calcined diatomaceous earth. The diatomaceous earth can be Celite® diatomaceous earth. Reaction conditions can include the presence of one or more activating agents such as platelet agonists (epinephrine, arachidonic acid, adenosine di-phosphate, collagen and additional components in the sample container, such as glass beads. Reaction conditions include the sample containers being subjected to one or more of a longitudinal rocking motion, lateral motion, and rotational motion in one or more directions.

The time to arrive at the platelet endpoints of clumping (platelet aggregation) and sticking (adhesion to the inner wall of the container) are shortened in samples with very active platelets and correspondingly lengthened in samples with inhibited platelets. The times required for platelet aggregation, adhesion to the inner wall of the container, and clotting endpoints are variably affected by platelet activity. Methods disclosed here allow for concurrent evaluation of platelet function and platelet-activated blood clotting. Other changes in the physical properties of the blood sample such as turbidity, viscosity, permittivity, and absorbance can also be measured to monitor and evaluate endpoints. Measurements of the optical density of the blood sample can also be used to monitor hemoglobin concentration.

The systems and reagent kits disclosed here support the methods of assessing the risk of bleeding or clotting both under normal healthy conditions and when the hemostasis mechanisms are stressed in an individual. The systems and reagent kits disclosed here support the methods of determining the platelet function and coagulation status of an individual, where a reference normal range is plus/minus two standard deviations around a midpoint, and beyond the two standard deviations, the individual is at risk for bleeding or clotting. The systems and reagent kit disclosed here also support the assessment of platelet function and coagulation within the normal reference range. The systems and reagent kits disclosed here support the methods of assessing hemostatic competence of an individual, who is a blood or blood product donor. The methods include determining the hemostatic status of the donor at an initial time point after sample acquisition and then at several subsequent times by subjecting the whole blood sample to analytical methods disclosed here.

Disclosed here are methods of combining the data from one or more endpoints to determine the hemostatic status of an individual. In an embodiment, the platelet response to one or more of four agonists—adenosine diphosphate, arachidonic acid, epinephrine and collagen—can be evaluated. In another embodiment, the set of agonists can include other agents, such as ristocetin. In another embodiment, a Bleeding Clotting Index (BCI) is determined by plotting the area under curve (AUC) for two endpoints—platelet adhesion to the inner wall of the sample container and clotting as these endpoints shorten with the disappearance of short-lived, circulating inhibitors of clotting and of platelet aggregation/adhesion. Table 1 presents the $AUC_{0-15}$ for thrombotic risk assessment. These values will change dependent on the type and amount of reagents used, changes in dilution of the blood sample, and the specific manufacture methods of the sample containers.

TABLE 1

$AUC_{0-15}$ for thrombotic risk assessment.

| $AUC_{0-15}$ | Adhesion of platelet aggregates | Clotting |
|---|---|---|
| AUC Mean | 2009.7 | 2277.3 |
| AUC Standard Deviation | 273.0 | 153.4 |
| AUC Ref range | 1464-2556 | 1971-2584 |

An individual is considered to have normal hemostatic status when the BCI (Z score value corresponding to $AUC_{0-15}$) of the individual for the adhesion of platelet aggregates and the clotting are within two standard deviations of the mean $AUC_{0-15}$ of the reference sample in Table 1. An individual is considered to have increased risk of clotting when the BCI ($AUC_{0-15}$) for the adhesion of platelet aggregates and the clotting is less than two standard deviations from the mean $AUC_{0-15}$ of the reference sample in Table 1. When the BCI ($AUC_{0-15}$) for the adhesion of platelet aggregates and the clotting are greater than two standard deviations of the $AUC_{0-15}$ of the reference sample in Table 1, the BCI determined under the $AUC_{0-60}$ is consulted for risk of bleeding. Table 2 presents the $AUC_{0-60}$ for thrombotic risk assessment. An individual is considered to have normal hemostasis status when the BCI (Z score value corresponding to $AUC_{0-60}$) for the adhesion of platelet aggregates and the clotting are within two standard deviations of the mean $AUC_{0-60}$ of the reference sample in Table 2. An individual is considered to have an increased risk of clotting when the BCI ($AUC_{0-60}$) for the adhesion of platelet aggregates and the clotting is less than two standard deviations of the mean $AUC_{0-60}$ of the reference sample in Table 2, and the BCI determined under the $AUC_{0-15}$ is consulted for risk of clotting. An individual is considered to have an increased risk of bleeding when the BCI ($AUC_{0-60}$) for the adhesion of platelet aggregates and the clotting is greater than two standard deviations of the mean $AUC_{0-60}$ of the reference sample in Table 2. These values will change dependent on the type and amount of reagents used, changes in dilution of the blood sample, and the specific manufacture methods of the sample containers.

TABLE 2

$AUC_{0-60}$ for thrombotic risk assessment

| $AUC_{0-60}$ | Adhesion of platelet aggregates | Clotting time |
|---|---|---|
| AUC Mean | 5758.5 | 8514.1 |
| AUC Standard Deviation | 1094.2 | 595.6 |
| AUC Ref range | 3570-7947 | 7323-9705 |

For example, if clotting analysis of a patient's sample reveals an $AUC_{0-15}$ of 2119 (Z score of −1.03) and $AUC_{0-60}$ of 7950 (Z score of −0.95), then there is no evidence of either an increased risk of bleeding or clotting. If platelet function analysis of a patient's sample reveals an $AUC_{0-15}$ of 1912 (Z score of −0.36) and $AUC_{0-60}$ of 5312 (Z score of −0.41), then there is no evidence of either an increased risk of bleeding or clotting. In another example, if clotting analysis of a patient's sample reveals an $AUC_{0-15}$ of 2978 (Z score of 4.57) and $AUC_{0-60}$ of 11915 (Z score of 5.71) and platelet function analysis of this patient's sample reveals an $AUC_{0-15}$ of 2978 (Z score of 3.55) and $AUC_{0-60}$ of 11915 (Z score of 5.63), then this patient is at an increased risk of bleeding. This pattern of clotting and platelet function was observed in a patient with atrial fibrillation, who was treated on a long term basis with Coumadin. In another example, if clotting analysis of a patient's sample reveals an $AUC_{0-15}$ of 2701 (Z score of 2.76) and $AUC_{0-60}$ of 10475 (Z score of 3.29) and platelet function analysis of this patient's sample reveals an $AUC_{0-15}$ of 2147 (Z score of 0.5) and $AUC_{0-60}$ of 5809 (Z score of 0.05), then this patient is at an increased risk of bleeding due to clotting issues despite no evidence of impaired platelet function. This pattern of clotting and platelet function was observed in a patient with atrial fibrillation, who was treated on a long term basis with Coumadin and aspirin but was recommended to halt Coumadin. In another example, if clotting analysis of a patient's sample reveals an $AUC_{0-15}$ of 1819 (Z score of −2.99) and $AUC_{0-60}$ of 6909 (Z score of −2.69) and platelet function analysis of this patient's sample reveals an $AUC_{0-15}$ of 1218 (Z score of −2.9) and $AUC_{0-60}$ of 3555 (Z score of −2.01), then this patient is at an increased thrombotic risk. This pattern of clotting and platelet function was observed in a patient with history of pulmonary embolism.

Another method of presenting data from one or more endpoints to determine the platelet function and coagulation status of an individual and provide decision support to a healthcare professional includes developing a bleeding risk profile (BRISK Profile). A BRISK profile is a graphical plot that includes an overlay of time-based monitoring of one or more endpoints, such as platelet aggregation, platelet adhesion to the inner wall of a sample container, and clotting.

This data presentation is performed in an operating room during surgery (for example during organ transplantation (most often during liver transplantation)) to determine whether disseminated intravascular coagulation (DIC) is present and, if the patient is bleeding, what transfusion modalities are likely to be most helpful.

Figure 12:
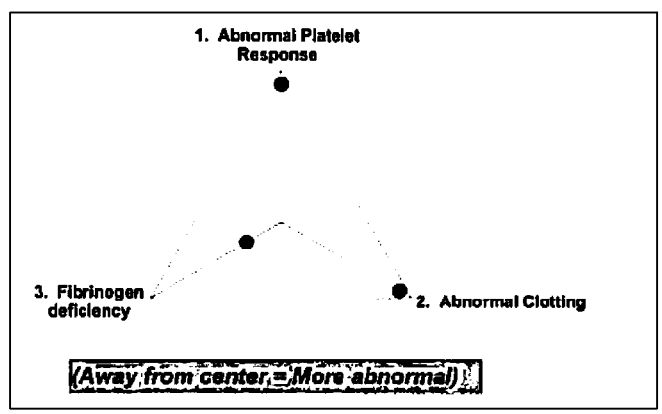
FIG. 12 is a star diagram that presents data from three endpoints measured by a system for platelet function and coagulation analysis according to one embodiment of the present disclosure.

A method of presenting data from one or more endpoints to determine the hemostatic status of an individual and provide decision support to a healthcare professional includes developing a star diagram. FIG. 12 is an example of a star diagram that presents data from BRISK profile and soluble fibrin assays as measured by a system for platelet function and coagulation analysis. In a star diagram, the fibrinogen deficiency, the clotting time, and the platelet function of a patient sample are plotted on the x, y, and z axis. The further a particular data point is from the origin, the more abnormal is that particular endpoint as compared to a reference sample from a healthy individual. In this example shown in FIG. 12, the platelet response and the clotting time are abnormal while the fibrinogen deficiency is comparatively less abnormal. If a patient is bleeding and a healthcare professional reviews this star diagram, then the healthcare professional may recommend a platelet transfusion based on the abnormal platelet response. He may also recommend fresh frozen plasma (FFP) as there is an indication of abnormally prolonged clotting. Depending on the extent of fibrinogen deficiency, he may also recommend a cryoprecipitate which contains a concentrated subset of FFP components including fibrinogen, Factor VIII coagulant, von Willebrand factor, and Factor XIII.

Embodiments of the methods and systems disclosed herein facilitate detection of soluble fibrin issues in Covid-19 patients. In severely ill patients, Covid-19 produces the diverse outcomes—damage to the heart, liver, kidneys, and brain, diarrhea, and skin lesions that look like frostbite—by partial expropriation of the clotting cascade. Other than the signs and symptoms of a viral pneumonitis, it may be this expropriation of clotting and the sequelae caused by this anomalous clotting that account for almost all of the findings in Covid-19 that are unexpected in a viral pneumonitis. Almost all severely ill patients show a marked rise in D-dimers, indicating that clotting has occurred somewhere in the body. As a result, heparin administration in (modest) prophylactic doses to all seriously ill ICU patients, has now become routine.

Several days into a severe Covid-19 infection, "exudate" macrophages that have assembled in response to a SARS-CoV-2 infection of alveolar lung epithelium attack and destroy the virally infected cells. In mouse models of lethal influenza virus pneumonia this "attack of the macrophages" occurs between the fifth and the seventh day of infection. A similar process takes place in Covid-19—a "bloodstream blizzard" of oligomeric (soluble) fibrin appears seven to ten days into Covid-19 pneumonia. In the animal viral pneumonitis model, where the macrophage attack occurs between day five and day seven, this event takes place two to three days after the influenza virus titer has peaked; it is, therefore, not a direct response to viral overload. However, once the "bloodstream blizzard" of oligomeric fibrin appears, the pathophysiology of Covid pneumonia is no longer primarily that of a viral disease; it is now largely that of a clotting disorder.

The immediate causative agent of this "bloodstream blizzard" is thrombin as this enzyme acts on fibrinogen to produce fibrin. The source of this thrombin in Covid-19 pneumonia is most likely thromboplastin (also known as Tissue Factor, TF) that has been generated when thromboplastin-rich alveolar macrophages destroy infected respiratory epithelium. Macrophage-initiated destruction of virally infected Type I epithelial cells, which line each alveolus, exposes the clotting enzymes present in blood to dead and dying pulmonary tissue rich in TF. Exposure of blood to TF activates the extrinsic clotting cascade; within a few seconds thrombin is the result. However, this activation of clotting is an atypical type, as it is distinguished by only rarely producing clinically evident clots. The atypical clotting appears to result from the repeated entrance of minute quantities of thrombin into the bloodstream. The minute quantity of the thrombin produced in each alveolus results in only a few molecules of fibrin before the thrombin is swept away and diluted by ongoing blood flow. For this reason, grossly detectable clots are rare, generally not visualized until autopsy. However, this unusual clotting process is capable of producing large amounts of circulating oligomeric-fibrin. And, as much of this oligomeric fibrin remains in solution—soluble fibrin, it is not currently detected and the patient is subject to inappropriate therapeutic interventions.

While the clotting is underway there are often no immediate clinical symptoms associated with it other than $O_2$ desaturation. Other clinical symptoms, if they are going to appear, will often not show up for hours or days. The lack of immediate clinical symptoms occurs because most of the fibrin molecules remain, like the antecedent fibrinogen molecules, in solution. The fibrin molecules are kept in solution by their small chain-length. Additionally, because the fibrin binding sites are complexed to complementary sites on native fibrinogen molecules, they are not readily accessible to other short-chain fibrin molecules. This inaccessibility slows the growth of fibrin protofibrils and the formation of fibrin clot. These molecular aggregates between short-chain fibrin and native fibrinogen molecules are known as Soluble Fibrin Monomer Complexes (referred to as soluble fibrin (SF)).

In only a minority of Covid-19 patients, the high levels of SF lead to the formation of large, branching, three-dimensional, fibrin polymers—polymers so large that they are no longer soluble and show up in the vasculature as clinically recognized macroscopic clots. More often even though some portion of the SF may have already achieved the size of fibrin protofibrils—macroscopically visible clots do not form. The clots that form are fragile, miniscule and, for the most part, rapidly dissolved by plasmin. The only evidence of their transient existence may be a rise in D-dimers over the next several hours. However, if a "bloodstream blizzard" of SF has supervened, the subsequent rise in D-dimers will not be subtle. Often it will be so extreme as to exceed the upper limits of the usually-reportable range for the D-dimer assay. In Covid-19 patients, D-dimers can remain at extremely high levels for 100 hours or more. Once this has occurred, death is extremely likely. However, it may often be delayed for days or weeks and the final diagnosis may appear unrelated to the pneumonia that initiated the rapid rise in SF.

A clinical situation involving SF is the disseminated intravascular coagulation (DIC) that can develop (fortunately briefly) in patients during liver transplantation surgery. If SF is going to appear at all, it will usually make its appearance just after reperfusion of the transplanted liver when residual dead and dying cells from the transplanted liver are washed into the recipient's vasculature. This is occasionally and catastrophically heralded by the sudden appearance of large clots in the heart and great vessels. If the newly transplanted liver is healthy and begins functioning immediately, the SF levels will generally drop back towards the normal range over the next 60 minutes or so.

A similar mechanism appears to be responsible for the generation of SF in patients with severe Covid-19 pneumonia. SARS-CoV-2 is a respiratory virus; it attacks respiratory epithelium. It typically causes necrosis of the infected cells as the cellular machinery is diverted to viral replication, and the host cell dies. Bleeding into the damaged alveolus exposes the enzymes of the coagulation cascade to Tissue Factor from the dead/dying alveolar cells. A brief micro-clotting episode occurs. Each micro-clotting episode produces a modest amount of thrombin and hence a small quantity of SF as it enters the pulmonary circulation and is whisked away. Because it is soluble, the SF that is produced will circulate throughout the body. The Covid-19 virus, having coopted a variant of clotting to produce SF, can now extend its damaging effects to the entire body. Wherever the SF molecules encounter other fibrin oligomers—due to conditions such as cooling in the extremities, vascular narrowing, roughened endothelium or other factors that result in turbulence or non-laminar flow, or simply extremely high levels of SF—the short chains of oligomeric fibrin can encounter one another, polymerize, lengthen and form two-stranded protofibrils that are 0.5-0.6 µm in length. These protofibrils correspond to ~20-25 monomers and are no longer soluble. Prior to this development, the monomers and shorter polymers have been held in soluble form while complexed to carrier fibrinogen molecules. Now, however, as the protofibrils lengthen, they become long enough to self-interact and aggregate laterally. A sol to gel transition occurs and microclots form. Even after gelation, new fibers and branching points continue to develop. As this process continues, the previously soluble SF now forms microclots, capable of occluding small blood vessels throughout the body. Most occlusions are rapidly cleared by clot lysis or by remodeling of the fibrin microclots prior to stabilization by Factor XIII But for those microclots that persist for more than several minutes, the tissue supplied by the occluded blood vessel, may die.

Embodiments of the methods and systems disclosed herein are used to detect SF that exists in the blood of certain Covid-pneumonia patients. Embodiments of the methods and systems disclosed herein are used for measurements of these oligomeric fibrin molecules in patients with severe Covid-19 pneumonia and analyze the process of SF formation that can result in whole body defibrination even though macro clots are not clinically or radiologically identified. The extremely high levels of SF will result in the formation of microclots throughout the vasculature which, together with ramped up fibrinolysis, leads directly to defibrination.

Embodiments disclosed here include methods of treating patients with Covid-19. In one such method, based on data about the levels of SF in patients with Covid-19 pneumonia, an anticoagulant is administered at a high therapeutic dose. In another method, based on data about the levels of SF in patients with Covid-19 pneumonia, a healthcare professional terminates any prophylactic (low dose) anticoagulant treatment that is being administered to the patient and initiates administration of higher doses of anticoagulant. In an embodiment, the anticoagulant treatment includes a heparinoid composition. The heparinoid composition can include one or more of heparin, heparan sulfate, low molecular weight heparins and heparin-like compounds. In an embodiment, an anticoagulant treatment includes enoxaparin. For example, the prophylactic (low dose) anticoagulant treatment can include 40 mg of orally active enoxaparin. An example of a higher dose of anticoagulant includes 80 to 120 mg of enoxaparin. An example of a higher dose of anticoagulant includes intravenous heparin sufficient to extend the partial thromboplastin time assay (an assay used to regulate anticoagulant dosages) to two and one half to three times the upper limit of the reference range. Normal levels of SF as measured by the methods described herein are 9 or less in males and 11 or less in females. In an embodiment, once the measurements of SF levels are above 25 or approximately two to two and one half times the normal values, as measured by the methods described herein, the patient is subject to an administration of therapeutic levels of anticoagulants. In an embodiment, a therapeutic level of anticoagulants is immediately administered to prevent the continued generation of SF and the transformation of SF into insoluble fibrin microclots throughout the patient's circulatory system. In an embodiment, the anticoagulant is a heparinoid composition. Heparin lengthens the clotting time of the Covid-19 patient and also facilitates the release of Tissue Factor Pathway Inhibitor (TFPI) from the lining of the blood vessels of the Covid-19 patient. Administration of heparin will significantly reduce SF production as TFPI interferes with the initiation of the extrinsic clotting cascade by TF produced in virally damaged and macrophage damaged lung alveoli.

In an embodiment, the patient has Covid-19 pneumonia with increased numbers of alveolar macrophages and significant damage to the lining cells of the lung alveoli such that Tissue Factor (thromboplastin) is being produced throughout the lungs. The method of treatment of such patient includes the step of determining whether gross clotting is ongoing by clinical examination and appropriate non-invasive methods for the detection of clots. Non-invasive methods can include ultrasound or optical detection systems. Non-invasive methods can include Doppler ultrasonic flow study, electrical impedance plethysmography, V/Q scanning, or a video capillaroscopy system. If patient does not exhibit any gross clotting, the method includes the step of measuring oligomeric fibrin levels in a blood sample. If oligomeric fibrin levels are more than 2-2.5 times elevated as compared to the normal values, the method includes the step of administering a therapeutic dose of an anticoagulant. If the patient is already under a prophylactic (low dose) anticoagulant treatment, then that treatment is terminated and administration of higher doses of anticoagulant is initiated. In an embodiment, the anticoagulant is heparin. A therapeutic dose of heparin is typically 3 fold or higher than the previously administered prophylactic heparin dose.

Embodiments disclosed here include methods of treating patients during the early viremic stage of Covid-19 with one or more antivirals targeting the SARS-CoV2 virus. These methods include the step of monitoring the soluble fibrin level of the patient and administering the one or more antivirals targeting the SARS-CoV2 virus. If Covid-19 transforms from a viral disease into a clotting disorder at, or about, the end of the first week of infection, one or more anticoagulants are administered. Antivirals would be appropriate while it is still only a viral pneumonitis. Anticoagulants are appropriate later in the illness, when SF levels begin to rise. In an embodiment, the antiviral is one or more of remdesivir, hydroxychloroquine, lopinavir, ritonavir, ribavirin, favipiravir, fluvoxamine, merimepodib, niclosamide, and interferon beta-lb. In an embodiment, hydroxychloroquine is administered along with zinc. In an embodiment, the antiviral is a monoclonal antibody targeting the SARS-CoV2 virus. In an embodiment, the anticoagulant includes a heparinoid composition. The heparinoid composition can include one or more of heparin and heparin-like compounds. In an embodiment, the anticoagulant is one or more of Coumadin, hirudin, and the oral anti Xa agents.

Examples

The hospital course of two patients are briefly summarized here as examples. Both patients were hospitalized in the early phases of the Covid-19 pandemic. As some form of clotting was assumed, these patients were already being placed on "prophylactic" (low dose) heparin. The first patient was admitted to a Covid-19 ICU with a blood level of less than 2.3 SFU. This patient was already on prophylactic heparin at the time the SFU levels were measured. Because of this low SF level, the patient was not tested again for three days. On the $4^{th}$ ICU day the SF was again tested and it had risen to 42.5 SFU, the fibrinogen had dropped from 686 mg/dl to 76 mg/dL and the D-Dimer level had risen to >21 µg/mL. The second patient was admitted to a Covid-19 ICU with a blood SF level of 8.2 SFU and a D-Dimer of 2.3 µg/mL. The next day the SF level had risen to 18 SFU and the D-Dimer level to 3.8. The day following, the SF was 45.8 and the D-Dimer was >21 µg/mL. Two days later the D-Dimer was still pegged at the upper limit of the reportable range (>21 µg/mL) and the SF had decreased somewhat to 28 SFU. Over that same 6-day period, the fibrinogen had dropped from 686 mg/dL to 89 mg/dL. These changes in the fibrinogen levels indicate that both of these patients essentially underwent defibrination as the level dropped from 686 to 76 mg/dL over 5 days in the first patient and from 686 to 89 mg/dL over 6 days in the second patient. Neither patient at any time showed evidence of gross clots (pulmonary emboli, deep vein thromboses, strokes or other evidence of major vessel occlusion).

A respiratory virus may be capable of damage to the heart, liver, kidneys, brain, and may bring on diarrhea and cause skin lesions that look like frostbite if that virus, by coopting the clotting system, is capable of generating large quantities of SF in the bloodstream. If the chain lengths of those fibrin molecules are short, and/or they are complexed to native fibrinogen so that they remain in solution, they have access to all parts of the body. SF, however, is certainly capable of damaging all cell types in the body via sporadic occlusion of portions of the microcirculation. While the presence of microclots in various tissue beds have been found in most patients during autopsy, their presence in extrapulmonary tissue in living Covid-19 ICU patients has been recently reported in a publication by Douglas Alexandre do Espirito Santo, Anna Cristina Bertoldi Lemos, and Carlos Henrique Miranda, titled "In vivo demonstration of microvascular thrombosis in severe COVID-19", in the Journal of Thrombosis and Thrombolysis (August 2020). Here, the sublingual microcirculation of 13 patients (on mechanical ventilation with markedly elevated D-Dimers but not meeting other criteria for DIC) was evaluated using a video, supravital, capillaroscopy system. Eleven patients (85%) percent demonstrated evidence of microvascular thrombosis, with 31% exhibiting completely stagnated capillaries. On three of the patients, an abrupt thromboembolic obstruction was captured on video as it occurred.

Given these findings the occurrence of potentially widespread 'invisible clots' may explain the beneficial effects of routine prophylactic heparin administration in COVID-19 patients. Therefore, when markedly elevated SF levels are detected, a method of treatment would include an immediate institution of therapeutic heparin levels. Failure to recognize the significance of elevated SF levels and respond appropriately may well result in whole or partial transformation of the body's store of fibrinogen into fibrin and the deposition of fibrin microclots throughout the body.

The foregoing description generally illustrates and describes various embodiments of the present invention. It will, however, be understood by those skilled in the art that various changes and modifications can be made to the above-discussed construction of the present invention without departing from the spirit and scope of the invention as disclosed herein, and that it is intended that all matter contained in the above description or shown in the accompanying drawings shall be interpreted as being illustrative, and not to be taken in a limiting sense.

Furthermore, the scope of the present disclosure shall be construed to cover various modifications, combinations, additions, alterations, etc., above and to the above-described embodiments, which shall be considered to be within the scope of the present invention. Accordingly, various features and characteristics of the present invention as discussed herein may be selectively interchanged and applied to other illustrated and non-illustrated embodiments of the invention, and numerous variations, modifications, and additions further can be made thereto without departing from the spirit and scope of the present invention as set forth in the appended claims.

We claim:

1. A system for analysis of blood samples, comprising:
a frame defining an analysis chamber;
   a sample analysis assembly received within the analysis chamber,
   the sample analysis assembly containing:
a carriage moveably supported within the analysis chamber;
   a sample container assembly mounted along the carriage and configured to receive at least one sample container containing a blood sample, the sample container assembly linked to a drive mechanism for rotating the at least one sample container;
   a lighting assembly including a light array arranged adjacent to the sample container assembly in a position to direct light of a selected intensity towards the at least one sample container; and
   a camera supported along the carriage at a location inside the sample container assembly, the camera configured to capture a plurality of images of the blood sample,
   wherein movement of the carriage causes the sample container assembly and the camera to move together in a substantially coordinated motion, and wherein the motion of the carriage and rotating of the at least one sample container provides a complex motion to the blood sample and is configured to facilitate platelet aggregation, platelet adhesion to the inner aspect of the sample container, or both.

2. The system of claim 1, wherein the camera comprises a video camera that captures a plurality of images.

3. The system of claim 1, further comprising a mirror mounted along the carriage in a position to receive and reflect the plurality of images of the blood sample within the at least one sample container; and wherein the camera receives the plurality of images of the blood sample reflected by the mirror.

4. The system of claim 1, wherein the lighting assembly further comprises at least one light shroud mounted in front of the light array and having a slit defined therealong, the at least one light shroud being movable so as to position its slit for directing the light from the light array toward a selected portion of the at least one sample container.

5. The system of claim 1, wherein the sample container assembly comprises upper and lower supports defining at least one recess along which the at least one sample container is received and supported, and a drive motor in communication with the at least one sample container to drive rotation thereof.

6. The system of claim 5, wherein the at least one sample container is received in a substantially horizontally oriented alignment along at least one recess, and wherein the camera is oriented in an alignment substantially facing the at least one sample container.

7. The system of claim 5, wherein the upper and lower supports are formed from a reduced friction polymer material.

8. The system of claim 1, wherein the light array of the lighting assembly comprises a series of light emitting diodes and at least one driver for controlling the selected intensity of the light supplied by the light emitting diodes.

9. The system of claim 8, wherein the light emitting diodes comprise a series of different color light emitting diodes configured to apply one or more different colors of light to the at least one sample container.

10. The system of claim 1, wherein the sample container assembly further comprises a series of disks arranged to engage the at least one sample container at spaced locations therealong, each of the disks comprising a reduced profile and linked to the drive mechanism to drive the rotation of the at least one sample container.

11. The system of claim 1, wherein the carriage comprises a platform moveably mounted within and extending along the analysis chamber, a series of upstanding supports configured to support the camera, the sample container assembly, and the light array, and an agitation mechanism linked to the platform and configured to impart a lateral rocking motion to the carriage and a longitudinal rocking motion to the at least one sample container.

12. An image analysis system for determining platelet function and coagulation status of a blood sample, comprising:
 a frame delivering an analysis chamber;
 a sample analysis assembly received within the analysis chamber,
 the sample analysis assembly containing:
  a carriage moveably supported within the analysis chamber;
  a sample container assembly mounted along the carriage and configured to receive at least one sample container containing a whole blood sample from the individual, the sample container assembly linked to a drive mechanism for rotating the at least one sample container;
  a lighting assembly including a light array arranged adjacent the sample container assembly in a position to direct light of a selected intensity and wavelength toward the at least one sample container;
  a camera supported along the carriage below the sample container assembly, the camera configured to capture a plurality of images of the blood sample,
   wherein movement of the carriage causes at least the sample container assembly and camera to move together in a substantially coordinated motion, and wherein the motion of the carriage and rotating of the at least one sample container provides one or more of a longitudinal rocking motion, lateral motion, or rotational motion in one or more directions to the blood sample therein; and
 a controller configured to process the plurality of images of the blood sample from the camera for identifying one or more endpoints of hemostasis occurring in the blood sample and determining hemostasis status of the individual in response to the identification of the one or more endpoints of hemostasis.

13. The image analysis system of claim 12, wherein the one or more endpoints of hemostasis is formation of soluble fibrin precipitates.

14. The image analysis system of claim 12, wherein the one or more endpoints of hemostasis is formation of platelet aggregates that are larger than 0.5 mm in diameter.

15. The image analysis system of claim 12, wherein the at least one sample container comprises a disposable tube.

16. The image analysis system of claim 12, wherein the light array of the lighting assembly comprises a series of light emitting diodes and at least one driver for controlling the selected intensity of the light supplied by the light emitting diodes.

17. The image analysis system of claim 16, wherein the light emitting diodes comprise a series of different color light emitting diodes configured to apply one or more different colors of light to the at least one sample container.

18. The image analysis system of claim 12, wherein the sample container assembly comprises upper and lower supports defining recesses in which the at least one sample container is received, and a drive mechanism including a drive motor coupled to a drive gear, wherein as the drive gear is rotated by the drive motor, the drive gear engages geared portions of the at least one sample container to drive rotation of the at least one sample container.

19. The image analysis system of claim 18, wherein the sample containers are received in a substantially horizontally oriented alignment along the recesses of the upper and lower supports, and wherein the camera is oriented in an alignment substantially facing the at least one sample container.

20. The image analysis system of claim 12, wherein the lighting assembly further comprises at least one light shroud mounted in front of the light array and having a slit defined there along, the at least one light shroud being movable with respect to the light array to direct the light from the light array through a selected portion of the whole blood sample in the at least one sample container.

* * * * *